(12) United States Patent
Wenzel et al.

(10) Patent No.: US 8,211,667 B2
(45) Date of Patent: Jul. 3, 2012

(54) FUNGAL PROMOTER FOR EXPRESSING A GENE IN A FUNGAL CELL

(75) Inventors: Thibaut José Wenzel, Leiden (NL); Noël Nicolaas Maria Elisabeth Van Peij, Delft (NL); Hein Stam, Huizen (NL)

(73) Assignee: DSM IP Assets B.V., TE Heerlen (NL)

( * ) Notice: Subject to any disclaimer, the term of this patent is extended or adjusted under 35 U.S.C. 154(b) by 523 days.

(21) Appl. No.: 11/578,514

(22) PCT Filed: Apr. 18, 2005

(86) PCT No.: PCT/EP2005/051696
§ 371 (c)(1),
(2), (4) Date: Mar. 12, 2007

(87) PCT Pub. No.: WO2005/100573
PCT Pub. Date: Oct. 27, 2005

(65) Prior Publication Data
US 2008/0305523 A1    Dec. 11, 2008

(30) Foreign Application Priority Data

| Apr. 16, 2004 | (EP) | 04076175 |
| Apr. 16, 2004 | (EP) | 04076176 |
| Apr. 16, 2004 | (EP) | 04076179 |
| Apr. 16, 2004 | (EP) | 04076180 |
| Apr. 16, 2004 | (EP) | 04076182 |

(51) Int. Cl.
*C12N 15/09*   (2006.01)
*C12N 15/00*   (2006.01)
*C12N 1/15*    (2006.01)
*C07H 21/04*   (2006.01)

(52) U.S. Cl. .............. 435/69.1; 435/320.1; 435/254.3; 435/254.5; 435/254.6; 536/23.1

(58) Field of Classification Search .......... None
See application file for complete search history.

(56) References Cited

FOREIGN PATENT DOCUMENTS
WO     99/32617     7/1999

OTHER PUBLICATIONS

International Search Report for PCT/EP2005/051696 mailed May 18, 2005.
N. Kitamoto et al. "Utilization of the TEF1-alpha gene (TEF1) promoter for expression of polygalacturonase genes, pgaA and pgaB, in *Aspergillus oryzae*" Applied Microbiology and Biotechnology, vol. 50, No. 1, pp. 85-92 (1998).
T. Fowler et al. "The catR gene encoding a catalase from *Aspergillus niger*: Primary structure and elevated expression through increased gene copy number and use of a strong promoter" Molecular Microbiology, vol. 9, No. 5, pp. 989-998 (1993).
A. Tsang et al. "An _2027 *Aspergillus niger*, pYES2 (XhoI-EcoRI) *Aspergillus niger* cDNA clone 2027 3', mRNA sequence" EMBL database, Accession No. BE760662 (2000).
I.N. Roberts et al. "Expression of the *Escherichia coli* beta-glucuronidase gene in industrial and phytopathogenic filamentous fungi" Current Genetics, vol. 15, No. 3, pp. 177-180 (1989).
P. Punt et al. "Intracellular and extracellular production of proteins in *Aspergillus* under the control of expression signals of the highly expressed *Aspergillus nidulans* gpdA gene" Journal of Biotechnology, vol. 17, No. 1, pp. 19-33 (1991).
J. Verdoes et al. "The effect of multiple copies of the upstream region on expression of the *Aspergillus niger* glucoamylase-encoding gene" Gene, vol. 145, No. 2, pp. 179-187 (1994).

*Primary Examiner* — Nancy Vogel
(74) *Attorney, Agent, or Firm* — Nixon & Vanderhye P.C.

(57) ABSTRACT

The present invention relates to isolated fungal promoter DNA sequences, to DNA constructs, vectors, and fungal host cells comprising these promoters in operative association with coding sequences encoding polypeptides. The present invention also relates to methods for expressing a gene and/or producing a polypeptide using the new promoters isolated. The present invention also relates to methods for altering the transcription level and/or regulation of an endogenous gene using the new promoter of the invention.

26 Claims, 8 Drawing Sheets

Promoter replacement of *glaA*

FUNGAL PROMOTER FOR EXPRESSING A GENE IN A FUNGAL CELL

This application is a U.S. national phase under 35 U.S.C. 371 of Intl Patent Application No. PCT/EP2005/051696 filed 18 Apr. 2005, which designated the U.S. and claimed priority benefit of EP 04076175.1, EP04076180.1, EP 04076182.7, EP 04076179.3 and EP 04076176.9 all of which were filed on 16 Apr. 2004; the entire contents of each of which are hereby incorporated by reference.

FIELD OF THE INVENTION

The present invention relates to DNA sequences, in particular isolated fungal promoters, and to DNA constructs, vectors, and fungal host cells comprising these promoters in operative association with coding sequences encoding polypeptides. The present invention also relates to methods for expressing a gene and/or producing a polypeptide.

BACKGROUND OF THE INVENTION

Production of a recombinant polypeptide in a fungal host cell is usually accomplished by constructing an expression cassette in which the DNA coding for the polypeptide is placed under the expression control of a promoter, suitable for the host cell. The expression cassette may be introduced into the host cell, by plasmid- or vector-mediated transformation. Production of the polypeptide may then be achieved by culturing the transformed host cell under inducing conditions necessary for the proper functioning of the promoter contained in the expression cassette.

For each fungal host cell, expression of a coding sequence which has been introduced into the fungal host by transformation and production of recombinant polypeptides encoded by this coding sequence requires the availability of functional promoters. Numerous promoters are already known to be functional in fungal host cells. There are examples of cross-species use of promoters: the promoter of the *Aspergillus nidulans* (*A. nidulans* gpdA gene is known to be functional in *Aspergillus niger* (*A. niger*) (J. Biotechnol. 1991 January; 17(1):19-33. Intracellular and extracellular production of proteins in *Aspergillus* under the control of expression signals of the highly expressed *A. nidulans* gpdA gene. Punt P J, Zegers N D, Busscher M, Pouwels P H, van den Hondel C A.) Another example is the *A. niger* beta-xylosidase xlnD promoter used in *A. niger* and *A. nidulans* Transcriptional regulation of the xylanolytic enzyme system of *Aspergillus*, van Peij, NNME, PhD-thesis Landbouwuniversiteit Wageningen, the Netherlands, ISBN 90-5808-154-0 and the expression of the *Escherichia coli* beta-glucuronidase gene in *A. niger*, *A. nidulans* and *Cladosporium fulvum* as described in Curr Genet. 1989 March; 15(3):177-80: Roberts I N, Oliver R P, Punt P J, van den Hondel C A. "Expression of the *Escherichia coli* beta-glucuronidase gene in industrial and phytopathogenic filamentous fungi".

However, there is still a need for improved promoters for controlling the expression of introduced genes, for controlling the level of expression of endogenous genes, for controlling the regulation of expression of endogenous genes or for mediating the inactivation of an endogenous gene, or for producing polypeptides, or for combination of the previous applications. These improved promoters may for example be stronger than the previous known ones. They may also be inducible by a specific convenient substrate or compound. Knowing several functional promoters is also an advantage when one envisages to simultaneously over express various genes in a single fungal host. To prevent squelching (titration of specific transcription factors), it is preferable to use multiple distinct promoters, one specific promoter for each gene to be expressed.

DETAILED DESCRIPTION OF THE INVENTION

Figure 1:
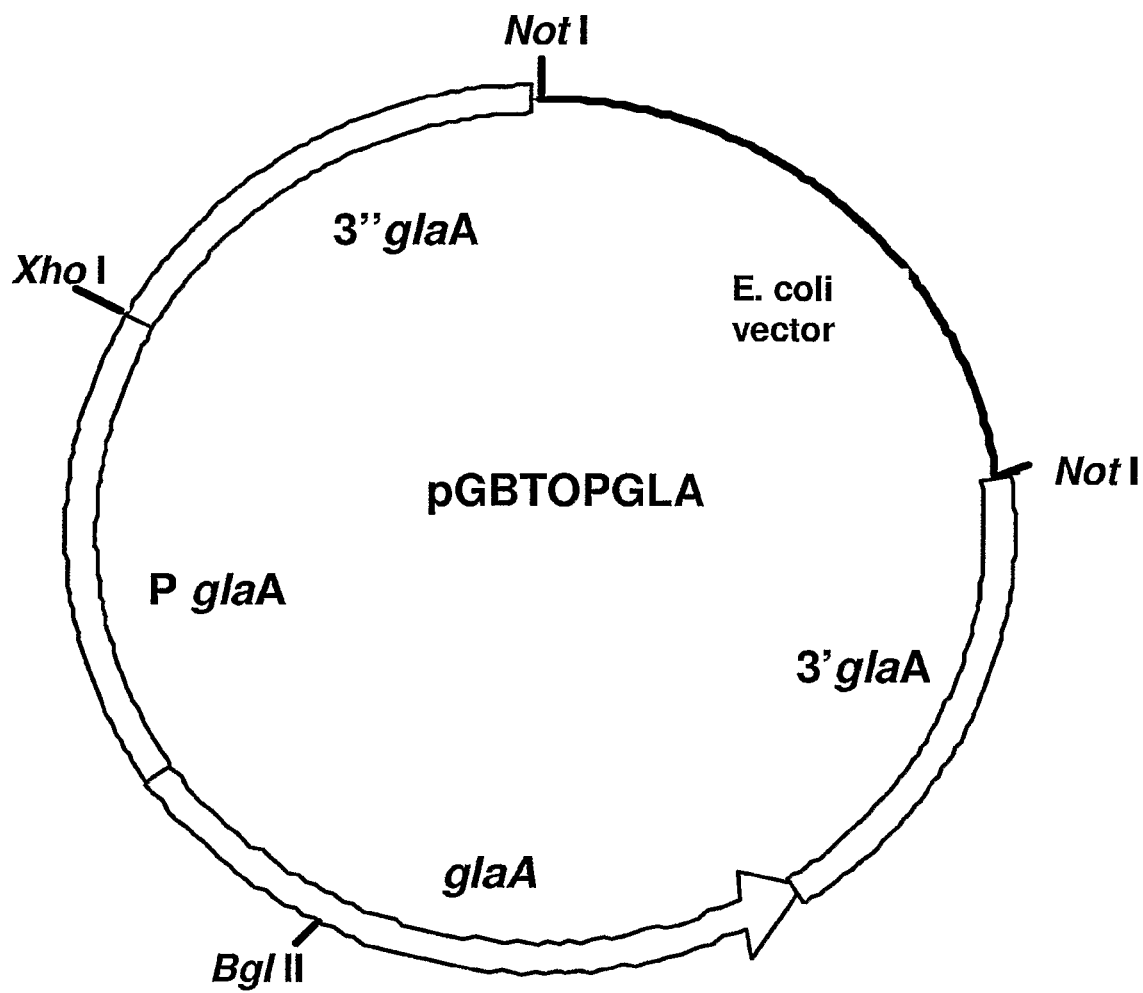
FIG. 1 depicts the plasmid map of pGBTOPGLA, which is an integrative glucoamylase expression vector.

The present invention relates to a promoter DNA sequence selected from the group consisting of:
(a) a DNA sequence comprising the nucleotide sequence of SEQ ID NO:1, SEQ ID NO:2, SEQ ID NO:3, SEQ ID NO:4, SEQ ID NO:5,
(b) a DNA sequence capable of hybridizing with a DNA sequence of (a),
(c) a DNA sequence being at least 50% homologous to a DNA sequence of (a),
(d) a variant of any of the DNA sequences of (a) to (c), and
(e) a subsequence of any of the DNA sequences of (a) to (d).

In the context of this invention, a promoter DNA sequence is a DNA sequence, which is capable of controlling the expression of a coding sequence, when this promoter DNA sequence is in operative association with this coding sequence. The term "in operative association" is defined herein as a configuration in which a promoter DNA sequence is appropriately placed at a position relative to a coding sequence such that the promoter DNA sequence directs the production of a polypeptide encoded by the coding sequence.

The term "coding sequence" is defined herein as a nucleic acid sequence that is transcribed into mRNA, which is translated into a polypeptide when placed under the control of the appropriate control sequences. The boundaries of the coding sequence are generally determined by the ATG start codon, which is normally the start of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences.

More specifically, the term "promoter" is defined herein as a DNA sequence that binds the RNA polymerase and directs the polymerase to the correct downstream transcriptional start site of a coding sequence encoding a polypeptide to initiate transcription. RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as enhancers, and other nucleotide sequences capable of interacting with transcription factors.

In a preferred embodiment, the promoter DNA sequence of the invention is a sequence according to SEQ ID NO:1, SEQ ID NO:2, SEQ ID NO:3, SEQ ID NO:4 or SEQ ID NO:5.

According to another preferred embodiment, the promoter DNA sequence of the invention is a DNA sequence capable of hybridizing with SEQ ID NO 1, SEQ ID NO:2, SEQ ID NO:3, SEQ ID NO:4 or SEQ ID NO:5, and which still retains promoter activity.

Promoter activity is preferably determined by measuring the concentration of the protein(s) coded by the coding sequence(s), which is (are) in operative association with the promoter. Alternatively the promoter activity is determined by measuring the enzymatic activity of the protein(s) coded by the coding sequence(s), which is (are) in operative association with the promoter. According to a preferred embodiment, the promoter activity (and its strength) is determined by measuring the expression of the coding sequence of the lacZ reporter gene (In Luo (Gene 163 (1995) 127-131. According to another preferred embodiment, the promoter activity is determined by using the green fluorescent protein as coding sequence (In Microbiology. 1999 March; 145 (Pt 3):729-34. Santerre Henriksen A L, Even S, Muller C, Punt P J, van den Hondel C A, Nielsen J. Study).

Additionally, promoter activity can be determined by measuring the mRNA levels of the transcript generated under control of the promoter. The mRNA levels can, for example, be measured through a Northern blot (J. Sambrook, E. F. Fritsch, and T. Maniatus, 1989, Molecular Cloning, A Laboratory Manual, 2d edition, Cold Spring Harbor, N.Y.).

The present invention encompasses (isolated) promoter DNA sequences that hybridize under very low stringency conditions, preferably low stringency conditions, more preferably medium stringency conditions, more preferably medium-high stringency conditions, even more preferably high stringency conditions, and most preferably very high stringency conditions with a nucleic acid probe that corresponds to (i) nucleotides 1 to 2000 of SEQ ID NO:1, SEQ ID NO:2, SEQ ID NO:3, SEQ ID NO:4 or SEQ ID NO:5, preferably nucleotides 100 to 1990, more preferably 200 to 1980, even more preferably 300 to 1970, even more preferably 350 to 1950 and most preferably 360 to 1900, (ii) is a subsequence of (i), or (iii) is a complementary strand of (i), (ii), (J. Sambrook, E. F. Fritsch, and T. Maniatis, 1989, Molecular Cloning, A Laboratory Manual, 2d edition, Cold Spring Harbor, N.Y.). The subsequence of SEQ ID NO:1, SEQ ID NO:2, SEQ ID NO:3, SEQ ID NO:4 or SEQ ID NO:5, may be at least 100 nucleotides, preferably at least 200 nucleotides, more preferably at least 300 nucleotides, even more preferably at least 400 nucleotides and most preferably at least 500 nucleotides.

The nucleic acid sequence of SEQ ID NO:1, SEQ ID NO:2, SEQ ID NO:3, SEQ ID NO:4 or SEQ ID NO:5 or a subsequence thereof may be used to design a nucleic acid probe to identify and clone DNA promoters from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Additionally, such probes can be used to amplify DNA promoters though PCR. An example of cloning a promoter through PCR is described herein (see example 1.3). Longer probes can also be used. DNA, RNA and Peptide Nucleid Acid (PNA) probes can be used. The probes are typically labelled for detecting the corresponding gene (for example, with @32 P, @33 P @3H, @35 S, biotin, or avidin or a fluorescent marker). Such probes are encompassed by the present invention.

Thus, a genomic DNA or cDNA library prepared from such other organisms may be screened for DNA, which hybridizes with the probes described above and which encodes a polypeptide. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1, SEQ ID NO:2, SEQ ID NO:3, SEQ ID NO:4 or SEQ ID NO:5, or a subsequence thereof, the carrier material may be used in a Southern blot.

For purposes of the present invention, hybridization indicates that the nucleic acid sequence hybridizes to a labeled nucleic acid probe corresponding to the nucleic acid sequence shown in SEQ ID NO:1, SEQ ID NO:2, SEQ ID NO:3, SEQ ID NO:4 or SEQ ID NO:5, their complementary strands, or subsequences thereof, under very low to very high stringency conditions. Molecules to which the nucleic acid probe hybridizes under these conditions are detected using for example a X-ray film. Other hybridisation techniques also can be used, such as techniques using fluorescence for detection and glass sides and/or DNA microarrays as support. An example of DNA microarray hybridisation detection is given in FEMS Yeast Res. 2003 December; 4(3):259-69 (Daran-Lapujade P, Daran J M, Kotter P, Petit T, Piper M D, Pronk J T. "Comparative genotyping of the Saccharomyces cerevisiae laboratory strains S288C and CEN.PK113-7D using oligonucleotide microarrays". Additionally, the use of PNA microarrays for hybridization is described in Nucleic Acids Res. 2003 Oct. 1; 31(19):e119 (Brandt O, Feldner J, Stephan A, Schroder M, Schnolzer M, Arlinghaus H F, Hoheisel J D, Jacob A. PNA microarrays for hybridisation of unlabelled DNA samples.)

In a preferred embodiment, the nucleic acid probe is the nucleic acid sequence of SEQ ID NO:1, SEQ ID NO:2, SEQ ID NO:3, SEQ ID NO:4 or SEQ ID NO:5. In another preferred embodiment, the nucleic acid probe is the sequence having nucleotides 20 to 1980 of SEQ ID NO:1, SEQ ID NO:2, SEQ ID NO:3, SEQ ID NO:4 or SEQ ID NO:5, more preferably nucleotides 500 to 1950 of SEQ ID NO 1, SEQ ID NO:2, SEQ ID NO:3, SEQ ID NO:4 or SEQ ID NO:5, even more preferably nucleotides 800 to 1920 of SEQ ID NO 1, SEQ ID NO:2, SEQ ID NO:3, SEQ ID NO:4 or SEQ ID NO:5, and most preferably nucleotides 900 to 1900 of SEQ ID NO 1, SEQ ID NO:2, SEQ ID NO:3, SEQ ID NO:4 or SEQ ID NO:5. Another preferred probe is the part of the DNA sequence before the transcription site.

For long probes of at least 100 nucleotides in length, very low to very high stringency conditions are defined as prehybridization and hybridization at 42 DEG C. in 5.times.SSPE, 0.3% SDS, 200.mu.g/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2.times.SSC, 0.2% SDS preferably at least at 45 DEG C. (very low stringency), more preferably at least at 50 DEG C. (low stringency), more preferably at least at 55 DEG C. (medium stringency), more preferably at least at 60 DEG C. (medium-high stringency), even more preferably at least at 65 DEG C. (high stringency), and most preferably at least at 70 DEG C. (very high stringency).

For short probes which are about 15 nucleotides to about 70 nucleotides in length, stringency conditions are defined as prehybridization, hybridization, and washing post-hybridization at 5 DEG C. to 10 DEG C. below the calculated Tm using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1.times.Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6.times.SCC plus 0.1% SDS for 15 minutes and twice each for 15 minutes using 6.times.SSC at 5 DEG C. to 10 DEG C. below the calculated Tm.

According to another preferred embodiment, SEQ ID NO 1, SEQ ID NO:2, SEQ ID NO:3, SEQ ID NO:4 or SEQ ID NO:5 is first used to clone the native gene, coding sequence or part of it, which is operatively associated with it. This can be done starting with either SEQ ID NO 1, SEQ ID NO:2, SEQ ID NO:3, SEQ ID NO:4 or SEQ ID NO:5, or a subsequence thereof as earlier defined and using this sequence as a probe. The probe is hybridised to a cDNA or a genomic library of a given host, either *Aspergillus niger* or any other fungal host as defined in this application. Once the native gene or part of it has been cloned, it can be subsequently used itself as a probe to clone homologous genes thereof derived from other fungi by hybridisation experiments as described herein.

In the context of the invention, a homologous gene means a gene, which is at least 50% homologous (identical) to the native gene. Preferably, the homologous gene is at least 55% homologous, more preferably at least 60%, more preferably at least 65%, more preferably at least 70%, even more preferably at least 75% preferably about 80%, more preferably about 90%, even more preferably about 95%, and most preferably about 97% homologous to the native gene.

The sequence upstream of the coding sequence of the homologous gene is a promoter encompassed by the present invention. Alternatively, the sequence of the native gene, coding sequence or part of it, which is operatively associated with a promoter of the invention can be identified by using SEQ ID NO 1, SEQ ID NO:2, SEQ ID NO:3, SEQ ID NO:4 or SEQ ID NO:5 or a subsequence thereof as earlier defined to search genomic databases using for example an alignment or BLAST algorithm as described herein. This identified sequence subsequently can be used to identify orthologues or homologous genes in any other fungal host as defined in this application. The sequence upstream the coding sequence of the identified orthologue or homologous gene is a promoter encompassed by the present invention.

According to another preferred embodiment, the promoter DNA sequence of the invention is a(n) (isolated) DNA sequence, which is at least 50% homologous (identical) to SEQ ID NO:1, SEQ ID NO:2, SEQ ID NO:3, SEQ ID NO:4 or SEQ ID NO:5. Preferably, the DNA sequence is at least 55% homologous, more preferably at least 60%, more preferably at least 65%, more preferably at least 70%, even more preferably at least 75% preferably about 80%, more preferably about 90%, even more preferably about 95%, and most preferably about 97% homologous to SEQ ID NO:1, SEQ ID NO:2, SEQ ID NO:3, SEQ ID NO:4 or SEQ ID NO:5.

For purposes of the present invention, the degree of homology (identity) between two nucleic acid sequences is preferably determined by the BLAST program. Software for performing BLAST analyses is publicly available through the National Center for Biotechnology Information (URL site Ncbi[dot]nlm[dot]nih[dot]gov. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89: 10915 (1989)) alignments (B) of 50, expectation (E) of 10, M=5, N=4, and a comparison of both strands.

In another preferred embodiment, the promoter is a subsequence of SEQ ID NO 1, SEQ ID NO:2, SEQ ID NO:3, SEQ ID NO:4 or SEQ ID NO:5, the subsequence still having promoter activity. The subsequence preferably contains at least about 100 nucleotides, more preferably at least about 200 nucleotides, and most preferably at least about 300 nucleotides.

In another preferred embodiment, a subsequence is a nucleic acid sequence encompassed by SEQ ID NO:1, SEQ ID NO:2, SEQ ID NO:3, SEQ ID NO:4 or SEQ ID NO:5 except that one or more nucleotides from the 5' and/or 3' end have been deleted, said DNA sequence still having promoter activity.

In another preferred embodiment, the promoter subsequence is a 'trimmed' subsequence, i.e. a sequence fragment which is upstream from translation start and/or from transcription start. An example of trimming a promoter and functionally analysing it is described in Gene. 1994 Aug. 5; 145 (2):179-87: the effect of multiple copies of the upstream region on expression of the *Aspergillus niger* glucoamylase-encoding gene. Verdoes J C, Punt P J, Stouthamer A H, van den Hondel C A).

In another embodiment of the invention, the promoter DNA sequence is a variant of SEQ ID NO 1, SEQ ID NO:2, SEQ ID NO:3, SEQ ID NO:4 or SEQ ID NO:5.

The term "variant" or "variant promoter" is defined herein as a promoter having a nucleotide sequence comprising a substitution, deletion, and/or insertion of one or more nucleotides of a parent promoter, wherein the variant promoter has more or less promoter activity than the corresponding parent promoter. The term "variant promoter" will encompass natural variants and in vitro generated variants obtained using methods well known in the art such as classical mutagenesis, site-directed mutagenesis, and DNA shuffling. A variant promoter may have one or more mutations. Each mutation is an independent substitution, deletion, and/or insertion of a nucleotide.

According to a preferred embodiment, the variant promoter is a promoter, which has at least a modified regulatory site as compared to the promoter sequence first identified (SEQ ID NO 1, SEQ ID NO:2, SEQ ID NO:3, SEQ ID NO:4 or SEQ ID NO:5). Such a regulatory site can be removed in its entirety or specifically mutated as explained above. The regulation of such promoter variant is thus modified so that for example it is no longer induced by glucose. Examples of such promoter variants and techniques on how to obtain them are described in EP 673 429 or in WO 94/04673. These patents are herewith incorporated by reference.

The promoter variant can be an allelic variant. An allelic variant denotes any of two or more alternative forms of a gene occupying the same chromosomal locus. Allelic variation arises naturally through mutation, and may result in polymorphism within populations. The variant promoter may be obtained by (a) hybridizing a DNA under very low, low, medium, medium-high, high, or very high stringency conditions with (i) SEQ ID NO:1, SEQ ID NO:2, SEQ ID NO:3, SEQ ID NO:4 or SEQ ID NO:5, (ii) a subsequence of (i) or (iii) a complementary strand of (i), (ii), and (b) isolating the variant promoter from the DNA. Stringency and wash conditions are as defined herein.

The promoter of the invention can be a promoter, whose sequence may be provided with linkers for the purpose of introducing specific restriction sites facilitating ligation of the promoter sequence with the coding region of the nucleic acid sequence encoding a polypeptide.

The sequence information as provided herein should not be so narrowly construed as to require inclusion of erroneously identified bases. The specific sequences disclosed herein can readily be used to isolate the original DNA sequence from a filamentous fungus, in particular *Aspergillus niger*, and be subjected to further sequence analyses thereby identifying sequencing errors.

Unless otherwise indicated, all nucleotide sequences determined by sequencing a DNA molecule herein were determined using an automated DNA sequencer. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

The person skilled in the art is capable of identifying such erroneously identified bases and knows how to correct for such errors.

The present invention encompasses functional promoter equivalents typically containing mutations that do not alter the biological function of the promoter it concerns. The term "functional equivalents" also encompasses orthologues of the *A. niger* DNA sequences. Orthologues of the *A. niger* DNA sequences are DNA sequences that can be isolated from other strains or species and possess a similar or identical biological activity.

The promoter sequences of the present invention may be obtained from microorganisms of any genus. For purposes of the present invention, the term "obtained from" as used herein in connection with a given source shall mean that the polypeptide is produced by the source or by a cell in which a gene from the source has been inserted.

The promoter sequences may be obtained from a fungal source, preferably from a yeast strain such as a *Candida, Hansenula, Kluyveromyces, Pichia, Saccharomyces, Schizosaccharomyces,* or *Yarrowia* strain, more preferably from a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* strain.

In another preferred embodiment, the promoter sequences are obtained from a filamentous fungal strain such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* strain, more preferably from an *Aspergillus aculeatus, Aspergillus awamori, Aspergillus foetidus, Aspergillus japonicus, A. nidulans, A. niger, Aspergillus oryzae (A. oryzae), Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* strain.

In another preferred embodiment, the promoter sequences are obtained from a *Fusarium bactridioides, Fusarium cerealls, Fusarium crookwellense, Fusarium culmorum, Fusarium graminearum, Fusarium graminum, Fusarium heterosporum Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum* strain.

It will be understood that for the aforementioned species, the invention encompasses the perfect and imperfect states, and other taxonomic equivalents, e.g., anamorphs, regardless of the species name by which they are known. Those skilled in the art will readily recognize the identity of appropriate equivalents. Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, promoter sequences according to the invention may be identified and obtained from other sources including microorganisms isolated from nature (e.g, soil, composts, water, etc.) using the above-mentioned probes. Techniques for isolating microorganisms from natural habitats are well known in the art. The nucleic acid sequence may then be derived by similarly screening a genomic DNA library of another microorganism. Once a nucleic acid sequence encoding a promoter has been detected with the probe(s), the sequence may be isolated or cloned by utilizing techniques which are known to those of ordinary skill in the art (see, e.g., Sambrook et al., 1989, supra).

In the present invention, the promoter DNA sequence may also be a hybrid promoter comprising a portion of one or more promoters of the present invention; a portion of a promoter of the present invention and a portion of another known promoter, e.g., a leader sequence of one promoter and the transcription start site from the other promoter; or a portion of one or more promoters of the present invention and a portion of one or more other promoters. The other promoter may be any promoter sequence, which shows transcriptional activity in the fungal host cell of choice including a variant, truncated, and hybrid promoter, and may be obtained from genes encoding extracellular or intracellular polypeptides either homologous or heterologous to the host cell. The other promoter sequence may be native or foreign to the nucleic acid sequence encoding the polypeptide and native or foreign to the cell.

As a preferred embodiment, important regulatory subsequences of the promoter identified can be fused to other 'basic' promoters to enhance their promoter activity (as for example described in Mol Microbiol. 1994 May; 12(3):479-90. Regulation of the xylanase-encoding xlnA gene of *Aspergillus tubigensis*. de Graaff L H, van den Broeck H C, van Ooijen A J, Visser J.).

Other examples of other promoters useful in the construction of hybrid promoters with the promoters of the present invention include the promoters obtained from the genes for *A. oryzae* TAKA amylase, *Rhizomucor miehei* aspartic proteinase, *A. niger* neutral alpha-amylase, *A. niger* acid stable alpha-amylase, *A. niger* or *Aspergillus awamori* glucoamylase (glaA), *A. niger* gpdA, *A. niger* glucose oxidase goxC, *Rhizomucor miehei* lipase, *A. oryzae* alkaline protease, *A. oryzae* triose phosphate isomerase, *A. nidulans* acetamidase, and *Fusarium oxysporum* trypsin-like protease (WO 96/00787), as well as the NA2-tpi promoter (a hybrid of the promoters from the genes for *A. niger* neutral alpha-amylase and *A. oryzae* triose phosphate isomerase), *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase, and mutant, truncated, and hybrid promoters thereof. Other useful promoters for yeast host cells are described by Romanos et al., 1992, Yeast 8: 423-488.

In the present invention, the promoter DNA sequence may also be a "tandem promoter". A "tandem promoter" is defined herein as two or more promoter sequences each of which is in operative association with a coding sequence and mediates the transcription of the coding sequence into mRNA.

The tandem promoter comprises two or more promoters of the present invention or alternatively one or more promoters of the present invention and one or more other known promoters, such as those exemplified above useful for the construction of hybrid promoters. The two or more promoter sequences of the tandem promoter may simultaneously promote the transcription of the nucleic acid sequence. Alternatively, one or more of the promoter sequences of the tandem promoter may promote the transcription of the nucleic acid sequence at different stages of growth of the cell or morphological different parts of the mycelia.

In the present invention, the promoter may be foreign to the coding sequence encoding a polypeptide of interest and/or to the fungal host cell. A variant, hybrid, or tandem promoter of the present invention will be understood to be foreign to a coding sequence encoding a polypeptide even if the wild-type promoter is native to the coding sequence or to the fungal host cell.

A variant, hybrid, or tandem promoter of the present invention has at least about 20%, preferably at least about 40%, more preferably at least about 60%, more preferably at least about 80%, more preferably at least about 90%, more preferably at least about 100%, even more preferably at least about 200%, most preferably at least about 300%, and even most preferably at least about 400% of the promoter activity of the promoter having SEQ ID NO:1, SEQ ID NO:2, SEQ ID NO:3, SEQ ID NO:4 or SEQ ID NO:5.

The invention further relates to a DNA construct comprising at least one promoter DNA sequence as defined above and a coding sequence in operative association with said promoter DNA sequence such that the coding sequence can be expressed under the control of the promoter DNA sequence in a given fungal host cell.

The coding sequence encodes a polypeptide that may be native or heterologous to the fungal host cell of interest.

The term "polypeptide" is not meant herein to refer to a specific length of the encoded product and, therefore, encompasses peptides, oligopeptides, and proteins. The term "heterologous polypeptide" is defined herein as a polypeptide, which is not native to the fungal cell, a native polypeptide in which modifications have been made to alter the native sequence, or a native polypeptide whose expression is quantitatively altered as a result of a manipulation of the fungal cell by recombinant DNA techniques. For example, a native polypeptide may be recombinantly produced by, e.g., placing the sequence encoding the polypeptide under the control of the promoter of the present invention to enhance expression of the polypeptide, to expedite export of a native polypeptide of interest outside the cell by use of a signal sequence, and to increase the copy number of a gene encoding the polypeptide normally produced by the cell. The fungal cell may contain one or more copies of the coding sequence encoding the polypeptide.

Preferably, the coding sequence encodes a peptide hormone or variant thereof, an enzyme, an intracellular protein, a protein involved in secretion process, a protein involved in folding process, a chaperone, a peptide amino acid transporter, a glycosylation factor, a transcription factor, a receptor or portion thereof, an antibody or portion thereof, or a reporter protein.

In a preferred embodiment, the polypeptide is secreted extracellularly.

In a more preferred embodiment, the polypeptide is an enzyme. Examples of enzymes are cellulases such as endoglucanases, β-glucanases, cellobiohydrolases or β-glucosidases; hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases; amylolytic enzymes; phosphatases such as phytases, esterase such as lipases, proteolytic enzyme, such as proteases, peptidases, oxidoreductases such as oxidases, transferases, or isomerases.

Alternatively, the coding sequence may encode an intracellular protein such as for example a chaperone or transcription factor. An example of this is described in Appl Microbiol Biotechnol. 1998 October; 50(4):447-54 ("Analysis of the role of the gene bipA, encoding the major endoplasmic reticulum chaperone protein in the secretion of homologous and heterologous proteins in black *Aspergilli*. Punt P J, van Gemeren I A, Drint-Kuijvenhoven J, Hessing J G, van Muijlwijk-Harteveld G M, Beijersbergen A, Verrips C T, van den Hondel C A). This can be used for example to improve the efficiency of a host cell as protein producer if this coding sequence, such as a chaperone or transcription factor, was known to be a limiting factor in protein production.

The coding sequence may also encode an enzyme involved in the synthesis of a primary or secondary metabolite, such as organic acids, carotenoids, (beta-lactam) antibiotics, vitamins.

The coding sequence encoding a polypeptide of interest may be obtained from any prokaryotic, eukaryotic, or other source.

Alternatively, the coding sequence may code for the expression of an antisense RNA and/or an RNAi (RNA interference) construct. An example of expressing an antisense-RNA is shown in Appl Environ Microbiol. 2000 February; 66(2):775-82. (Characterization of a foldase, protein disulfide isomerase A, in the protein secretory pathway of *Aspergillus niger*. Ngiam C, Jeenes D J, Punt P J, Van Den Hondel C A, Archer D B) or (Zrenner R, Willmitzer L, Sonnewald U. Analysis of the expression of potato uridinediphosphate-glucose pyrophosphorylase and its inhibition by antisense RNA. Planta. (1993);190(2):247-52.) Complete inactivation of the expression of a gene is useful for instance for the inactivation of genes controlling undesired side branches of metabolic pathways, for instance to increase the production of specific secondary metabolites such as (beta-lactam) antibiotics or carotenoids. Complete inactivation is also useful to reduce the production of toxic or unwanted compounds (chrysogenin in *Penicillium*; Aflatoxin in *Aspergillus*: MacDonald K D et al,: heterokaryon studies and the genetic control of penicillin and chrysogenin production in *Penicillium chrysogenum*. J Gen Microbiol. (1963) 33:375-83). Complete inactivation is also useful to alter the morphology of the organism in such a way that the fermentation process and down stream processing is improved.

Another embodiment of the invention relates to the extensive metabolic reprogramming or engineering of a fungal cell. Introduction of complete new pathways and/or modification of unwanted pathways will provide a cell specifically adapted for the production of a specific compound such as a protein or a metabolite.

In the methods of the present invention, when the coding sequence codes for a polypeptide, said polypeptide may also include a fused or hybrid polypeptide in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptide may comprise a combination of partial or complete polypeptide sequences obtained from at least two different polypeptides wherein one or more may be heterologous to the fungal cell.

The DNA construct may comprise one or more control sequences in addition to the promoter DNA sequence, which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion. One or more control sequences may be native to the coding sequence or to the host. Alternatively, one or more control sequences may be replaced with one or more control sequences foreign to the nucleic acid sequence for improving expression of the coding sequence in a host cell.

"DNA construct" is defined herein as a nucleic acid molecule, either single or double-stranded, which is isolated from a naturally occurring gene or which has been modified to contain segments of nucleic acid combined and juxtaposed in a manner that would not otherwise exist in nature. The term DNA construct is synonymous with the term expression cassette when the DNA construct contains a coding sequence and all the control sequences required for expression of the coding sequence.

The term "control sequences" is defined herein to include all components, which are necessary or advantageous for the expression of a coding sequence, including the promoter of the invention. Each control sequence may be native or foreign to the nucleic acid sequence encoding the polypeptide. Such control sequences include, but are not limited to, a leader, an optimal translation initiation sequence (as described in Kozak, 1991, J. Biol. Chem. 266:19867-19870), a polyadenylation sequence, a propeptide sequence, a signal peptide sequence, an upstream activating sequence, the promoter of the invention including variants, fragments, and hybrid and tandem promoters derived thereof and a transcription terminator. At a minimum, the control sequences include transcriptional and translational stop signals and (part of) the promoter of the invention. The control sequences may be provided with linkers for the purpose of introducing specific restriction sites facilitating ligation of the control sequences with the coding region of the nucleic acid sequence encoding a polypeptide.

The control sequence may be a suitable transcription terminator sequence, i.e. a sequence recognized by a host cell to terminate transcription. The terminator sequence is in operative association with the 3' terminus of the coding sequence encoding the polypeptide. Any terminator, which is functional in the host cell of choice may be used in the present invention.

Preferred terminators for filamentous fungal host cells are obtained from the genes for *A. oryzae* TAKA amylase, *A. niger* glucoamylase, *A. nidulans* anthranilate synthase, *A. niger* alpha-glucosidase, trpC gene, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al, 1992, supra.

The control sequence may also be a suitable leader sequence, i.e. a 5' nontranslated region of a mRNA which is important for translation by the host cell. The leader sequence is in operative association with the 5' terminus of the nucleic acid sequence encoding the polypeptide. Any leader sequence that is functional in the host cell of choice may be used in the present invention.

Preferred leaders for filamentous fungal host cells are obtained from the genes for *A. oryzae* TAKA amylase, *A. nidulans* triose phosphateisomerase and *A. niger* glaA.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence in operative association with the 3' terminus of the nucleic acid sequence and which, when transcribed, is recognized by the host cell as a signal to add polyadenosine residues to transcribed mRNA. Any polyadenylation sequence, which is functional in the host cell of choice may be used in the present invention.

Preferred polyadenylation sequences for filamentous fungal host cells are obtained from the genes for *A. oryzae* TAKA amylase, *A. niger* glucoamylase, *A. nidulans* anthranilate synthase, *Fusarium oxysporum* trypsin-like protease, and *A. niger* alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *A. oryzae* TAKA amylase, *A. niger* neutral amylase, *A. ficuum* phytase, *A. niger* glucoamylase, *A. niger* endoxylanase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, *Myceliophthora thermophila* laccase (WO 95/33836) and *A. niger* endoxylanase (endo1).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, and trp operator systems. In yeast, the ADH2 system or GALL system may be used. In filamentous fungi, the TAKA alpha-amylase promoter, *A. niger* glucoamylase promoter, *A. oryzae* glucoamylase promoter, *A. tubingensis* endoxylanase (xlnA) promoter, *A. niger* nitrate reductase (niaD) promoter, *Trichoderma reesei* cellobiohydrolase promoter and the *A. nidulans* alcohol and aldehyde dehydrogenase (alcA and aldA, respectively) promoters as described in U.S. Pat. No. 5,503,991) may be used as regulatory sequences. Other examples of regulatory sequences are those, which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the polypeptide would be in operative association with the regulatory sequence.

Important can be removal of creA binding sites (carbon catabolite repression as described earlier in EP 673 429), change of pacC and areA (for pH and nitrogen regulation).

The present invention also relates to recombinant expression vectors comprising a promoter of the present invention, a coding sequence encoding a polypeptide, and transcriptional and translational stop signals. The various coding and control sequences described above may be joined together to produce a recombinant expression vector which may include one or more convenient restriction sites to allow for insertion or substitution of the promoter and/or coding sequence encoding the polypeptide at such sites: Alternatively, fusion of coding sequence and promoter can be done by e.g. sequence overlap extension using PCR (SOE-PCR), as described in Gene. 1989 Apr. 15; 77(1):51-9. Ho S N, Hunt H D, Horton R M, Pullen J K, Pease L R "Site-directed mutagenesis by overlap extension using the polymerase chain reaction") or by cloning using the Gateway™ cloning system (Invitrogen). Alternatively, the coding sequence may be expressed by inserting the coding sequence or a DNA construct comprising the promoter and/or coding sequence into an appropriate vector for expression. In creating the expression vector, the coding sequence is located in the vector so that the coding sequence is in operative association with a promoter of the present invention and one or more appropriate control sequences for expression.

The recombinant expression vector may be any vector (e.g., a plasmid or virus), which can be conveniently subjected to recombinant DNA procedures and can bring about the expression of the coding sequence. The choice of the vector will typically depend on the compatibility of the vector with the host cell into which the vector is to be introduced. The vectors may be linear or closed circular plasmids.

The vector may be an autonomously replicating vector, i.e., a vector, which exists as an extrachromosomal entity, the replication of which is independent of chromosomal replication, e.g., a plasmid, an extrachromosomal element, a minichromosome, or an artificial chromosome. For autonomous replication, the vector may comprise an origin of replication enabling the vector to replicate autonomously in the host cell in question. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, Proceedings of the National Academy of Sciences USA 75:1433). An example of an autonomously maintained cloning vector in a filamentous fungus is a cloning vector comprising the AMA1-sequence. AMA1 is a 6.0-kb genomic DNA fragment isolated from *A. nidulans*, which is capable of Autonomous Maintenance in *Aspergillus* (see e.g. Aleksenko and Clutterbuck (1997), Fungal Genet. Biol. 21: 373-397).

Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers, which permit easy selection of transformed cells. The host may be co-transformed with at least two vectors, one comprising the selection marker. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Marker conferring resistance against e.g. phleomycin, hygromycin B or G418 can also be used. Preferred for use in an *Aspergillus* cell are the amdS and pyrG genes of *A. nidulans* or *A. oryzae* and the bar gene of *Streptomyces hygroscopicus*. The amdS marker gene is preferably used applying the technique described in EP 635 574 or WO 97/0626. A preferred selection marker gene is the *A. nidulans* amdS coding sequence fused to the *A. nidulans* gpdA promoter (EP635 574). AmdS genes from other filamentous fungus may also be used (WO 97/06261).

For integration into the host cell genome, the vector may rely on the promoter sequence and/or coding sequence encoding the polypeptide or any other element of the vector for stable integration of the vector into the genome by homologous or non-homologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, more preferably 800 to 1,500 base pairs, and most preferably at least 2 kb, which are highly homologous with the corresponding target sequence to enhance the probability of homologous recombination. The integrational elements may be any 15 sequence that is homologous with the target sequence in the genome of the host cell. Furthermore, the integrational elements may be non-encoding or encoding nucleic acid sequences. In order to promote targeted integration, the cloning vector is preferably linearized prior to transformation of the host cell. Linearization is preferably performed such that at least one but preferably either end of the cloning vector is flanked by sequences homologous to the target locus.

Preferably, the integrational elements in the cloning vector, which are homologous to the target locus are derived from a highly expressed locus meaning that they are derived from a gene, which is capable of high expression level in the fungal host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (as described in EP 357 127 B1). A number of preferred highly expressed fungal genes are given by way of example: the amylase, glucoamylase, alcohol dehydrogenase, xylanase, glyceraldehyde-phosphate dehydrogenase or cellobiohydrolase genes from *Aspergilli* or *Trichoderma*. Most preferred highly expressed genes for these purposes are a glucoamylase gene, preferably an *A. niger* glucoamylase gene, an *A. oryzae* TAKA-amylase gene, an *A. nidulans* gpdA gene, the loci of SEQ ID NO:1, SEQ ID NO:2, SEQ ID NO:3, SEQ ID NO:4 or SEQ ID NO:5, the *A. niger* locus of SEQ ID NO: 1, SEQ ID NO:2, SEQ ID NO:3, SEQ ID NO:4 or SEQ ID NO:5, or a *Trichoderma reesei* cellobiohydrolase gene.

On the other hand, the vector may be integrated into the genome of the host cell by non-homologous recombination.

More than one copy of a nucleic acid sequence encoding a polypeptide may be inserted into the host cell to increase production of the gene product. This can be done, preferably by integrating into its genome copies of the DNA sequence, more preferably by targeting the integration of the DNA sequence at a highly expressed locus, preferably at a glucoamylase locus or at the locus of SEQ ID NO:1, SEQ ID NO:2, SEQ ID NO:3, SEQ ID NO:4 or SEQ ID NO:5. Alternatively, this can be done by including an amplifiable selectable marker gene with the nucleic acid sequence where cells containing amplified copies of the selectable marker gene, and thereby additional copies of the nucleic acid sequence, can be selected for by cultivating the cells in the presence of the appropriate 15 selectable agent. To increase even more the number of copies of the DNA sequence to be over expressed the technique of gene conversion as described in WO98/46772 may be used.

The procedures used to ligate the elements described above to construct the recombinant expression vectors of the present invention are well known to one skilled in the art (see, e.g., Sambrook et al., 1989, supra).

The present invention also relates to recombinant host cells, comprising a promoter DNA sequence of the present invention in operative association with a coding sequence encoding a polypeptide, which are advantageously used in the production of the polypeptides. A vector comprising a promoter of the present invention in operative association with a coding sequence encoding a polypeptide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The present invention also relates to recombinant host cells, comprising more than one promoter DNA sequence of the present invention, each promoter being in operative association with a coding sequence encoding a polypeptide. Such host cells may be advantageously used in the recombinant production of at least one polypeptide. Preferably at least one promoter and its associated coding sequence are present on a vector. The vector is introduced into a host cell so that it is maintained as a chromosomal integrant and/or as a self-replicating extra-chromosomal vector as described earlier.

According to another preferred embodiment, the host cell is used for the production of specific primary or secondary metabolites such as (beta-lactam) antibiotics, vitamins or carotenoids.

The host cell may be any fungal cell useful in the methods of the present invention. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (*Endomycetales*), basidiosporogenous yeast, and yeast belonging to the Fungi Imperfecti (*Blastomycetes*). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In a more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, or *Trichoderma*.

In a most preferred embodiment, the filamentous fungal host cell is an *Aspergillus awamori, Aspergillus foetidus, Aspergillus japonicus, A. nidulans, A. niger* or *A. oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatun, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, Proceedings of the National Academy of Sciences USA 81: 1470-1474. Suitable procedures for transformation of *Aspergillus* and other filamentous fungal host cells using *Agrobacterium tumefaciens* are described in e.g. Nat Biotechnol. 1998 September; 16(9):839-42. Erratum in: Nat Biotechnol 1998 November; 16(11):1074. *Agrobacterium tumefaciens*-mediated transformation of filamentous fungi. de Groot M J, Bundock P, Hooykaas P J, Beijersbergen A G. Unilever Research Laboratory Vlaardingen, The Netherlands. Suitable methods for transforming *Fusarium* species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75:1920.

The invention further relates to a method for expression of a coding sequence in a host cell. The method comprises the following steps:
 (a) providing a DNA construct comprising the promoter DNA sequence of the invention and the coding sequence as described above,
 (b) transforming a suitable host cell with said DNA construct and
 (c) expressing the coding sequence under the control of said promoter DNA sequence.

The invention also relates to a method for production of a polypeptide encoded by a coding sequence that is under control of the promoter of the invention in a suitable fungal host. The method comprises the following steps:
 (a) providing a DNA construct comprising the promoter DNA sequence of the invention and the coding sequence encoding the polypeptide as defined above,
 (b) transforming a suitable fungal host cell with said DNA construct,
 (c) culturing the suitable fungal host under suitable culture conditions conducive to expression of the polypeptide,
 (d) recovering the polypeptide from the culture broth.

The invention also relates to a method for production of a secondary metabolite in a suitable host comprising:
 (a) providing a DNA construct comprising the promoter DNA sequence of the invention and a coding sequence encoding an enzyme involved in the production of a secondary metabolite as described above,
 (b) transforming a suitable host cell with said DNA construct,
 (c) culturing the suitable fungal host under suitable culture conditions conducive to production of the secondary metabolite, and
 (d) recovering the secondary metabolite from the culture broth.

In the production methods of the present invention, the cells are cultivated in a nutrient medium suitable for production of the polypeptide or metabolite using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the coding sequence to be expressed and/or the polypeptide to be isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide or metabolite is secreted into the nutrient medium, the polypeptide or metabolite can be recovered directly from the medium. If the polypeptide or metabolite is not secreted, it can be recovered from cell lysates.

The polypeptides may be detected using methods known in the art that are specific for the polypeptides. These detection methods may include use of specific antibodies, formation of an enzyme product, or disappearance of an enzyme substrate.

The resulting polypeptide or metabolite may be recovered by methods known in the art. For example, the polypeptide or metabolite may be recovered from the nutrient medium by conventional procedures including, but not limited to, centrifugation, filtration, extraction, spray-drying, evaporation, or precipitation.

Polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

The present invention also relates to DNA constructs for altering the expression of a coding sequence encoding a polypeptide, which is endogenous to a fungal host cell. The constructs may contain the minimal number of components necessary for altering expression of the endogenous gene.

In one embodiment, the nucleic acid constructs preferably contain (a) a targeting sequence, (b) a promoter DNA sequence of the present invention, (c) an exon, and (d) a splice-donor site. Upon introduction of the nucleic acid construct into a cell, the construct integrates by homologous recombination into the cellular genome at the endogenous gene site. The targeting sequence directs the integration of elements (a)-(d) into the endogenous gene such that elements (b)-(d) are in operative association with the endogenous gene.

In another embodiment, the nucleic acid constructs contain (a) a targeting sequence, (b) a promoter DNA sequence of the present invention, (c) an exon, (d) a splice-donor site, (e) an intron, and (f) a splice-acceptor site, wherein the targeting sequence directs the integration of elements (a)-(f) such that elements (b)-(f) are in operative association with the endogenous gene. However, the constructs may contain additional components such as a selectable marker. The selectable markers that can be used were earlier described.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence, which causes the gene to be expressed at higher levels than evident in the corresponding parent cell.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The constructs further contain one or more exons of the endogenous gene. An exon is defined as a DNA sequence, which is copied into RNA and is present in a mature mRNA molecule such that the exon sequence is in-frame with the coding region of the endogenous gene. The exons can, optionally, contain DNA, which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged. The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence, which directs the splicing of one exon to another exon. Acting in conjunction with a splice-donor site, the splicing apparatus uses a splice-acceptor site to effect the removal of an intron.

A preferred strategy for altering the expression of a given DNA sequence comprises the deletion of the given DNA sequence and/or replacement of the endogenous promoter sequence of the given DNA sequence by a modified promoter DNA sequence, such as a promoter of the invention. The deletion and the replacement are preferably performed by the gene replacement technique described in EP 0 357 127. The specific deletion of a gene and/or promoter sequence is pref-erably performed using the amdS gene as selection marker gene as described in EP 635 574. By means of counterselection on fluoracetamide media as described in EP 635 574, the resulting strain is selection marker free and can be used for further gene modifications.

Alternatively or in combination with other mentioned techniques, a technique based on in vivo recombination of cosmids in E. coli can be used, as described in: A rapid method for efficient gene replacement in the filamentous fungus A. nidulans (2000) Chaveroche, M-K., Ghico, J-M. and d'Enfert C; Nucleic acids Research, vol 28, no 22. This technique is applicable to other filamentous fungi like for example A. niger. The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

All patents and publications, including all sequences and methods disclosed within such patents and publications, referred to herein are expressly incorporated by reference. These patents and publications include: EP 357 127, EP 673 429, EP 635 574, WO 97/06261, WO 98/46772, WO 94/04673.

EXAMPLES

Experimental Information

Strains

WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (glaA). WT 2 was constructed by using the "MARKER-GENE FREE" approach as described in EP 0 635 574. In this patent it is extensively described how to delete glaA specific DNA sequences in the genome of CBS 513.88. The procedure resulted in a MARKER-GENE FREE ?glaA recombinant *A. niger* CBS513.88 strain, possessing finally no foreign DNA sequences at all.

Glucoamylase Activity Assay

The glucoamylase activity was determined using p-Nitrophenyl a-D-glucopyranoside (Sigma) as described in WO 98/46772.

Example 1

Construction of a DNA Construct Comprising a Promoter of the Invention in Operative Association with a Coding Sequence This example describes the construction of an expression construct under control of a promoter of the invention. The coding sequence or reporter construct used here is the glaA gene encoding the *A. niger* glucoamylase enzyme. Glucoamylase is used as the reporter enzyme to be able to measure the activity of the promoter of the invention.

1.1 Description of an Integrative Glucoamylase Expression Vector (pGBTOPGLA)

The glucoamylase promoter and the glucoamylase encoding gene glaA from *A. niger* were cloned into the expression vector pGBTOP-8, which is described in WO99/32617. The cloning was performed according known principles and to routine cloning techniques and yielded plasmid pGB-TOPGLA (see FIG. 1). In essence, this expression vector comprises the glucoamylase promoter, coding sequence and terminator region, flanked by the 3' and 3" glaA targeting sites in an *E. coli* vector.

1.2 Construction of an Integrative Glucoamylase Expression Vector with a Multiple Cloning Site MCS (pGBTOPGLA-2)

Figure 2:
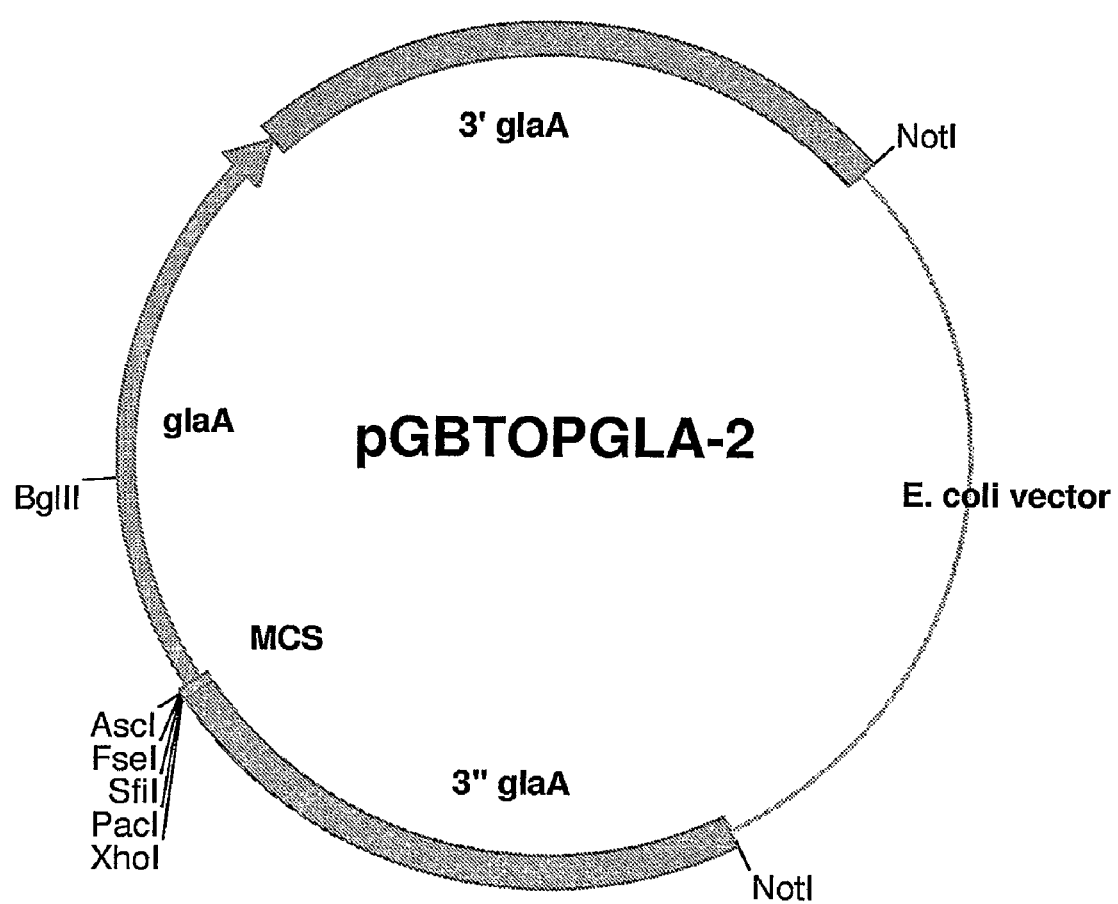
FIG. 2 depicts the plasmid map of pGBTOPGLA-2, which is an integrative glucoamylase expression vector with a multiple cloning site.

Using the Oligonucleotides
5'-ATgCggCCgCCTCgAgTTAATTAAggC-CAggCCggCCggCgCgCCTCAgCAATgTCgTTCCgA-3'
identified as SEQ ID NO 6 and
5'-AGCCATTGACTTCTTCCCAG-3'
identified as SEQ ID NO 7 and 1 ng of vector pGB-TOPGLA as a template, a PCR fragment was generated containing part of the glaA coding sequence. This fragment was digested with XhoI and BglII and introduced in XhoI and BglII digested vector pGBTOPGLA, resulting in vector pGBTOPGLA-2 (see FIG. 2). The sequence of the introduced PCR fragment comprising a MCS and part of the glaA coding sequence was confirmed by sequence analysis.

1.3 Construction of an Integrative Expression Vector with the Promoter of the Invention in Operative Association with the Glucoamylase Coding Sequence (pGBTOPGLA-3)

Figure 3:
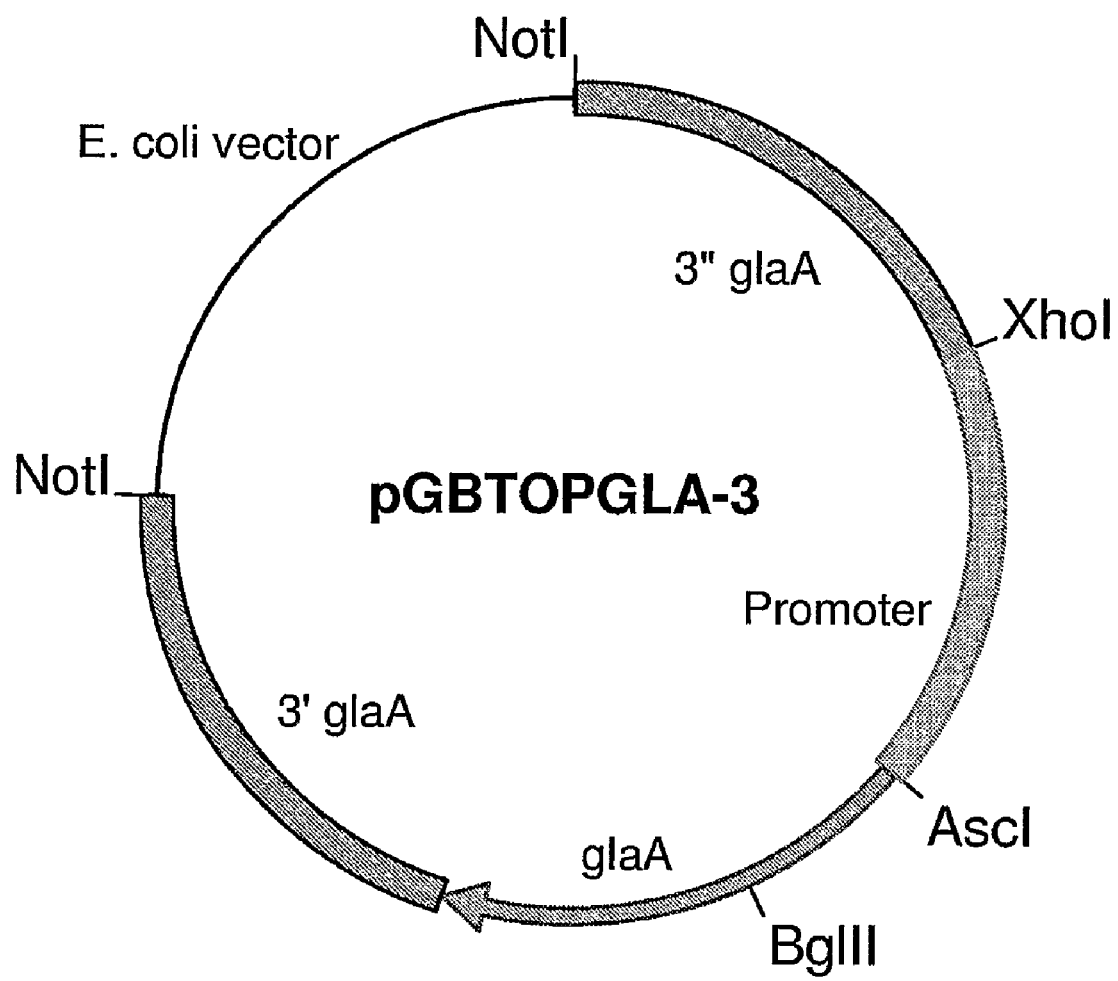
FIG. 3 depicts the plasmid map of pGBTOPGLA-3, which is an integrative expression vector containing the promoter of the invention in operative association with the glucoamylase coding sequence.

Genomic DNA of strain CBS513.88 was sequenced and analysed. Using the oligonucleotide combinations as identified below (Oligo SEQ ID NO's) in the Table and genomic DNA of strain CBS513.88 as template, appropriate restriction sites were attached to the promoter of the invention by PCR amplification. The sequences as identified in SEQ ID NO 1, SEQ ID NO:2, SEQ ID NO:3, SEQ ID NO:4 or SEQ ID NO:5 comprise the sequences of the resulting fragments of about 2 kb, as indicated in the Table below. All five resulting fragments were digested with AscI and XhoI and introduced in AscI and XhoI digested vector pGBTOPGLA-2, resulting in vector pGBTOPGLA-4, pGBTOPGLA-5, pGBTOPGLA-7, GBTOPGLA-9 or pGBTOPGLA-10, as indicated in the Table (Vector name). In FIG. 3, a picture can be found which is illustrative for the layout of all five vectors. The sequence of the various introduced PCR fragments comprising the promoters of the invention was confirmed by sequence analysis.

| Oligo SEQ ID NO: | Oligo SEQ ID NO: | Vector name | SEQ ID NO: of promoter cloned in vector |
|---|---|---|---|
| 8 | 9 | pGBTOPGLA-7 | 1 |
| 10 | 11 | pGBTOPGLA-9 | 2 |
| 12 | 13 | pGBTOPGLA-4 | 3 |
| 14 | 15 | pGBTOPGLA-10 | 4 |
| 16 | 17 | pGBTOPGLA-5 | 5 |

Example 2

Fungal Host Cell Transformed with the DNA Construct

In order to introduce the pGBTOPGLA, pGBTOPGLA-4, pGBTOPGLA-5, pGBTOPGLA-7, pGBTOPGLA-9 or pGBTOPGLA-10 vectors in WT 2, a transformation and subsequent transformant selection was carried out as described in WO98/46772 and WO99/32617. In principle, linear DNA of all vectors was isolated after digestion with NotI and co-transformed with an amdS selectable marker-gene containing vector, which is designated pGBAAS-1 (constructed as described in EP 635574). Both vectors comprise two DNA domains homologous to the glaA locus of *A. niger* host strain to direct targeting to the truncated glaA locus in WT 2. Transformants were selected on acetamide media and colony purified according standard procedures. Spores were plated on fluoro-acetamide media to select strains, which lost the amdS marker. Growing colonies were diagnosed for integration at the glaA locus and copy number. Transformants of pGB-TOPGLA, pGBTOPGLA-4, pGBTOPGLA-5, pGB-TOPGLA-7, pGBTOPGLA-9 or pGBTOPGLA-10 with similar estimated copy numbers were selected. Preferably, few transformants with a single copy (1A, 1B, 1C) and possibly one with multiple copies (2A) were selected.

Figure 4:
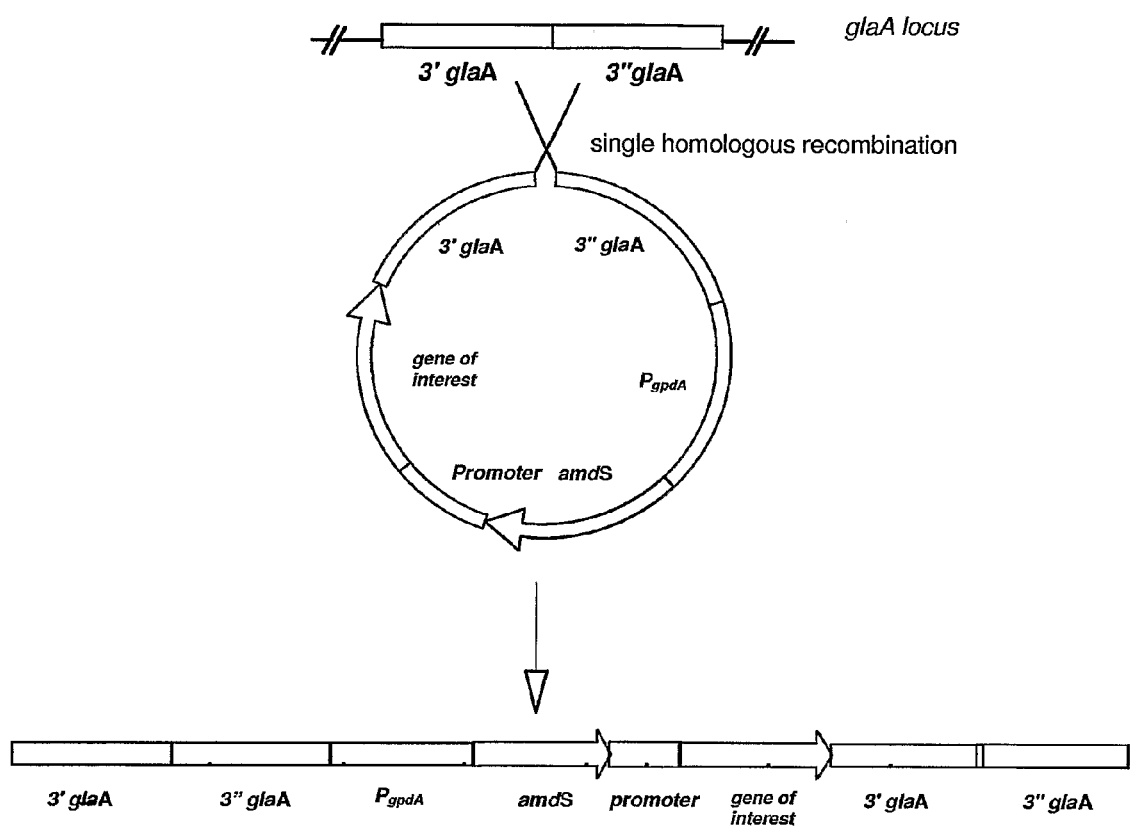
FIG. 4 depicts a schematic representation of integration through single homologous recombination.

Additionally, the selectable marker gene and the gene of interest controlled by a promoter of the invention would have been on one construct. An example of this is shown in FIG. 4.

Example 3

Figure 5:
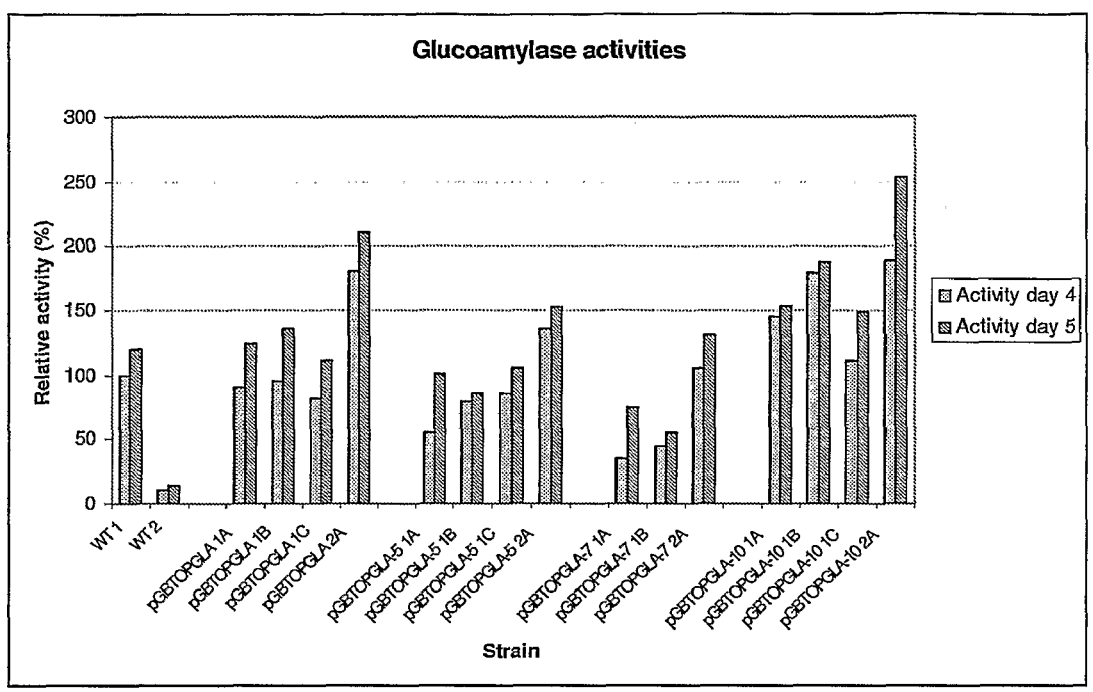
FIG. 5: Glucoamylase activities of WT 1, WT 2 and transformants of various pGBTOPGLA vectors. Normalised activities are shown, where the activity of WT 1 at day 4 was set at 100%.

Production of the Glucoamylase Polypeptide Encoded by the glaA Coding Sequence Under Control of a Promoter of the Invention in the Fungal Host Cell A number of selected transformants of WT 2, as described above, and both strains WT 1 and WT 2 were used to perform shake flask experiments in 100 ml of the medium as described in EP 635 574 at 34° C. and 170 rpm in an incubator shaker using a 500 ml baffeled shake flask. After 4 and 5 days of fermentation, samples were taken to determine the glucoamylase activity, as described above. The glucoamylase activities were normalised to the activity of WT 1 on day 4. The normalised activities of WT 1, WT 2 and a number of selected transformants for of pGBTOPGLA, pGBTOPGLA-5, pGB-TOPGLA-7, and pGBTOPGLA-10 are indicated in FIG. 5

As can be concluded from the measured activities of the glucoamylase reporter, the invention provides a strong promoter for high expression of a gene of interest in a fungal cell. As such, the promoters of the invention provide alternative and additional promoters for high expression of a gene of interest in a fungal cell.

Example 4

Construction of a Promoter Replacement Construct pGBDEL-PGLAA Comprising a Promoter of the Invention To alter the expression level of a given gene in a host cell, a promoter of the invention can replace the endogenous promoter of said given gene. In this example, a promoter of the invention replaces the promoter of the glucoamylase encoding glaA gene in a fungal host cell. Examples 4, 5 and 6 describe a number of different steps in this process.

Figure 6:
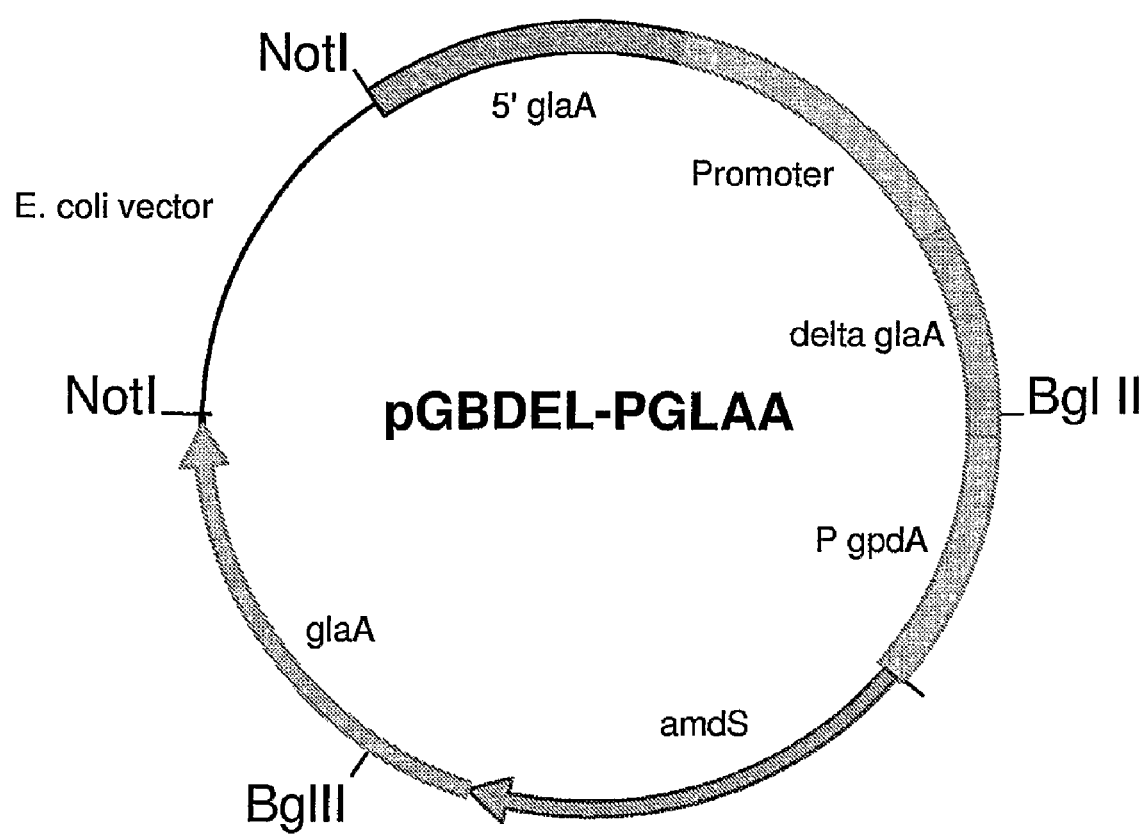
FIG. 6 depicts the plasmid map of pGBDEL-PGGLAA, which is a replacement vector.

A replacement vector for the glucoamylase promoter was designed according to known principles and constructed according to routine cloning procedures (see FIG. 6). In essence, the glaA promoter replacement vector pGBDEL-PGLAA comprises approximately 1000 bp flanking regions of the glaA promoter sequence to be replaced by a promoter of the invention, which is comprised by SEQ ID NO: 4, trough homologous recombination at the predestined genomic locus.

The flanking regions used here (see FIG. 6) are a 5' upstream region of the glaA promoter and part of the glaA coding sequence. In addition, the replacement vector contains the *A. nidulans* bi-directional amdS selection marker, in-between direct repeats. The direct repeats used in this example are part of the glaA coding sequence. The general design of these deletion vectors were previously described in EP635574 and WO 98/46772.

Example 5

Figure 7:
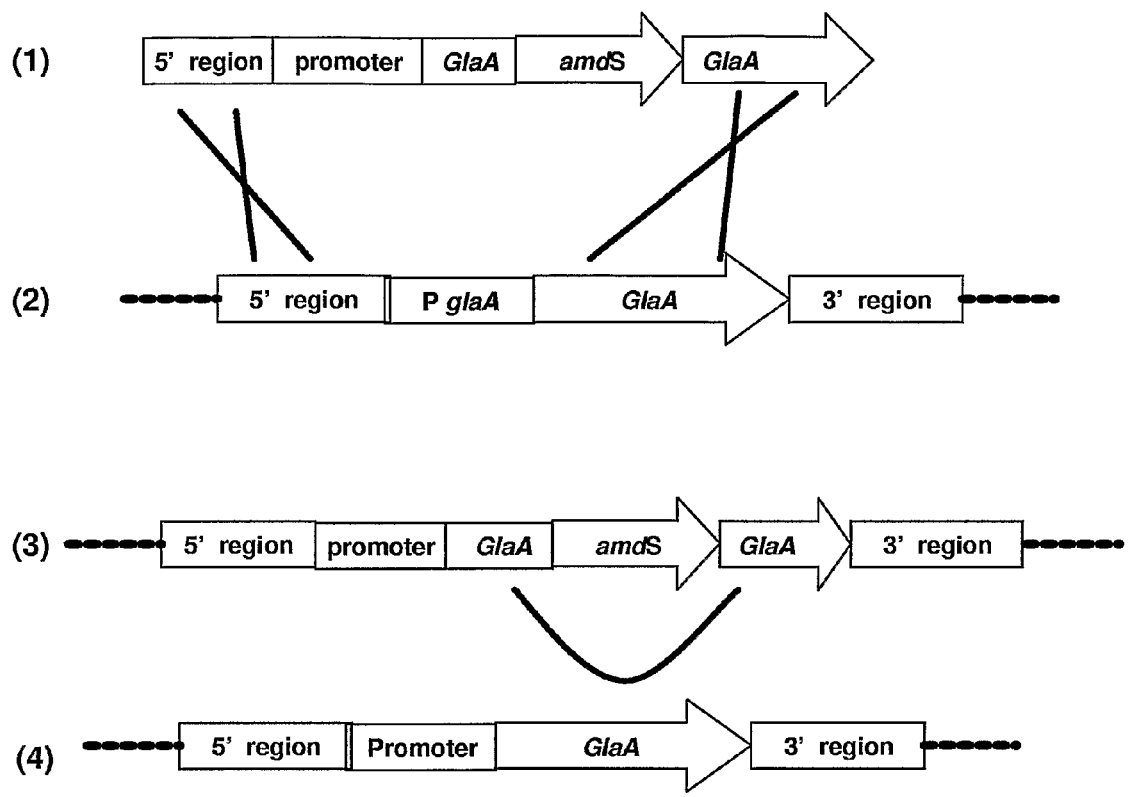
FIG. 7 depicts a schematic representation of a promoter replacement.

Replacement of the glaA Promoter by a Promoter of the Invention in the Fungal Host Cell Linear DNA of NotI-digested deletion vector pGBDEL-PGLAA was isolated and used to transform WT 1 (CBS513.88). This linear DNA can integrate into the genome at the glaA locus, thus substituting the glaA promoter region with the construct containing amdS and a promoter of the invention (see FIG. 7). Transformants were selected on acetamide media and colony purified according to standard procedures. Growing colonies were diagnosed by PCR for integration at the glaA locus. Deletion of the glaA promoter was detectable by amplification of a band, with a size specific for the promoter of the invention and loss of a band specific for the glaA promoter. Spores were plated on fluoro-acetamide media to select strains, which lost the amdS marker. Candidate strains were testing using Southern analysis for proper deletion of the glucoamylase promoter and replacement by a promoter of the invention, as comprised by SEQ ID NO: 4. Strains dPGLAA were selected as representative strains with the glaA promoter replaced by the promoter of the invention and having a restored functional glaA coding sequence (see FIG. 7).

Example 6

Production of the Glucoamylase Polypeptide Encoded by the glaA Coding Sequence Under Control of a Replaced Promoter of the Invention, in the Fungal Host Cell The selected dPGLAA strains (proper pGBDEL-PGLM transformants of WT 1, isolated in example 5) and strain WT 1 were used to perform shake flask experiments in 100 ml of the medium as described in EP 635 574 B1 at 34° C. and 170 rpm in an incubator shaker using a 500 ml baffeled shake flask. Further conditions and activity measurements were as described in Example 3. The glucoamylase activity in the selected pGBDEL-PGLM transformants of WT1 was increased compared to the one measured for WT 1 at both days of fermentation (data not shown).

Example 7

Addition of an Additional glaA Gene Under Control of a Promoter of the Invention in the Fungal Host Cell To alter the expression level of a given gene in a host cell, multiple additional copies of said gene operatively linked to a promoter of the invention can be added to the endogenously given gene. In this example, a promoter of the invention, as comprised by SEQ ID NO: 4 and operatively linked with the glaA coding sequence is introduced next to the endogenously present glucoamylase encoding glaA gene in a fungal host cell. Example 7 and 8 describe a number of different steps in this process.

Figure 8:
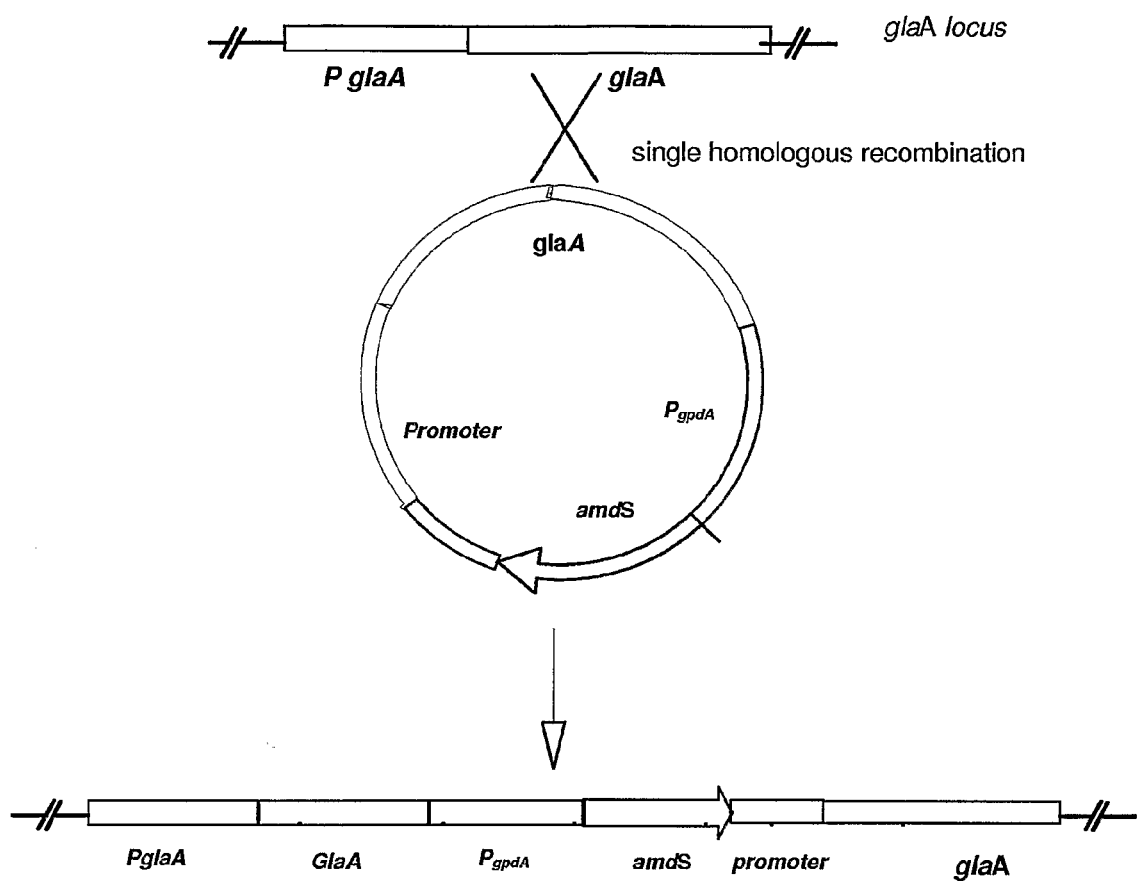
FIG. 8 depicts a schematic representation of integration through homologous recombination.

A circular construct as depicted in FIG. 8 was isolated and used to transform WT 1 (CBS513.88). This linear DNA can integrate into the genome at the glaA coding sequence, thus adding a second glaA gene under control of a promoter of the invention next to the selectable marker amdS (see FIG. 8). Transformants were selected on acetamide media and colony purified according to standard procedures. Growing colonies were diagnosed by PCR for integration at the glaA locus. Integration at the glaA locus was detected by PCR and Southern analysis. Strains P2GLAA were selected as representative strains with at least a second glaA gene under control of a promoter of the invention integrated at the glaA locus.

Example 8

Production of the Glucoamylase Polypeptide Encoded by the glaA Coding Sequences Under Control of a Promoter of the Invention and the Endogenous glaA Promoter in the Fungal Host Cell The selected P2GLAA strains, isolated in example 7, and strain WT 1 were used to perform shake flask experiments in 100 ml of the medium as described in Example 3. After 4 and 6 days of fermentation, samples were taken to determine the glucoamylase activity. The glucoamylase activity in the selected P2GLAA transformants of WT1 was increased compared to the one measured for WT 1 after either four or five days of fermentation. The increased activities of the glucoamylase reporter indicate that the promoters of the invention provide a means to further increase the expression of a gene of interest which is already expressed under a strong promoter in a fungal cell.

The invention claimed is:

1. An isolated DNA sequence selected from the group consisting of:
   (a) a DNA sequence comprising SEQ ID NO:4,
   (b) a DNA sequence capable of hybridizing to the complement of the full length sequence of SEQ ID NO:4 under high stringency conditions of 42° C., 5×SSPE, 0.3% SDS, 200µg/ml sheared and denatured salmon sperm DNA, and 50% formamide followed by washing three times each for 15 minutes using 2×SSC, 0.2% SDS at 60° C., and
   (c) a DNA sequence that is at least 97% identical to SEQ ID NO:4 along the full length of SEQ ID NO:4;
   said isolated DNA sequence having promoter activity.

2. A recombinant DNA construct comprising a DNA sequence according to claim 1 and a coding sequence in operative association with said DNA sequence such that the coding sequence can be expressed under control of the DNA sequence.

3. A method for expression of a gene comprising:
   (a) providing the DNA construct according to claim 2 wherein the coding sequence comprises a gene,
   (b) transforming a suitable host cell with said DNA construct, and
   (c) expressing the gene under control of said DNA sequence in the transformed host cell.

4. A method for production of a polypeptide comprising:
   (a) providing the DNA construct according to claim 2 comprising a coding sequence encoding the polypeptide,
   (b) transforming a suitable host cell with said DNA construct,
   (c) culturing the transformed host cell under conditions conducive to expression of the polypeptide, and
   (d) recovering the polypeptide from culture broth.

5. A method for production of a secondary metabolite comprising:
   (a) providing the DNA construct according to claim 2 comprising a coding sequence encoding an enzyme involved in the production of a secondary metabolite,
   (b) transforming a suitable host cell with said DNA construct,
   (c) culturing the transformed host cell under conditions conducive to production of the secondary metabolite, and
   (d) recovering the secondary metabolite from culture broth.

6. A host cell comprising the DNA construct according to claim 2.

7. The host cell according to claim 6, wherein the host cell is an *Aspergillus, Penicillium* or *Trichoderma* species.

8. The host cell according to claim 7, wherein the host cell is an *Aspergillus niger* or *Aspergillus oryzae* species.

9. The isolated DNA sequence of claim 1 wherein said sequence is the DNA sequence comprising SEQ ID NO:4.

10. A recombinant DNA construct comprising a DNA sequence according to claim 9 and a coding sequence in operative association with said DNA sequence such that the coding sequence can be expressed under control of the DNA sequence.

11. A host cell comprising the DNA construct according to claim 10.

12. The host cell according to claim 11, wherein the host cell is an *Aspergillus, Penicillium* or *Trichoderma* species.

13. The host cell according to claim 12, wherein the host cell is an *Aspergillus niger* or *Aspergillus oryzae* species.

14. A method for expression of a gene comprising:
    (a) providing the DNA construct according to claim 10 wherein the coding sequence comprises a gene,
    (b) transforming a suitable host cell with said DNA construct, and
    (c) expressing the gene under control of said DNA sequence in the transformed host cell.

15. A method for production of a polypeptide comprising:
    (a) providing the DNA construct according to claim 10 comprising a coding sequence encoding the polypeptide,
    (b) transforming a suitable host cell with said DNA construct,
    (c) culturing the transformed host cell under conditions conducive to expression of the polypeptide, and
    (d) recovering the polypeptide from culture broth.

16. A method for production of a secondary metabolite comprising:
    (a) providing the DNA construct according to claim 10 comprising a coding sequence encoding an enzyme involved in the production of a secondary metabolite,
    (b) transforming a suitable host cell with said DNA construct,
    (c) culturing the transformed host cell under conditions conducive to production of the secondary metabolite, and
    (d) recovering the secondary metabolite from culture broth.

17. A recombinant expression vector comprising (i) a DNA sequence according to claim 9, (ii) a coding sequence in operative association with said DNA sequence such that the coding sequence can be expressed under control of the DNA sequence as a promoter and (iii) transcriptional and translational stop signals.

18. A host cell comprising the expression vector according to claim 17.

19. A method for expression of a gene comprising:
    (a) providing the expression vector according to claim 17 wherein the coding sequence comprises a gene,
    (b) transforming a suitable host cell with said expression vector, and
    (c) expressing the gene under control of said promoter in the transformed host cell.

20. A method for production of a polypeptide comprising:
    (a) providing the expression vector according to claim 17 comprising a coding sequence encoding the polypeptide,
    (b) transforming a suitable host cell with said expression vector,
    (c) culturing the transformed host cell under conditions conducive to expression of the polypeptide, and
    (d) recovering the polypeptide from culture broth.

21. A method for production of a secondary metabolite comprising:
    (a) providing the expression vector according to claim 17 comprising a coding sequence encoding an enzyme involved in the production of a secondary metabolite,
    (b) transforming a suitable host cell with said expression vector,
    (c) culturing the transformed host cell under conditions conducive to production of the secondary metabolite, and
    (d) recovering the secondary metabolite from culture broth.

22. A recombinant expression vector comprising (i) a DNA sequence according to claim 1, (ii) a coding sequence in operative association with said DNA sequence such that the coding sequence can be expressed under control of the DNA sequence as a promoter and (iii) transcriptional and translational stop signals.

23. A host cell comprising the expression vector according to claim 22.

24. A method for expression of a gene comprising:
    (a) providing the expression vector according to claim 22 wherein the coding sequence comprises a gene,
    (b) transforming a suitable host cell with said expression vector, and
    (c) expressing the gene under control of said promoter in the transformed host cell.

25. A method for production of a polypeptide comprising:
    (a) providing the expression vector according to claim 22 comprising a coding sequence encoding the polypeptide,
    (b) transforming a suitable host cell with said expression vector,
    (c) culturing the transformed host cell under conditions conducive to expression of the polypeptide, and
    (d) recovering the polypeptide from culture broth.

26. A method for production of a secondary metabolite comprising:
    (a) providing the expression vector according to claim 22 comprising a coding sequence encoding an enzyme involved in the production of a secondary metabolite,
    (b) transforming a suitable host cell with said expression vector,
    (c) culturing the transformed host cell under conditions conducive to production of the secondary metabolite, and
    (d) recovering the secondary metabolite from culture broth.

* * * * *

SEQUENCE LISTING

<160> NUMBER OF SEQ ID NOS: 17

<210> SEQ ID NO 1
<211> LENGTH: 2000
<212> TYPE: DNA
<213> ORGANISM: Aspergillus niger

<400> SEQUENCE: 1
ttttccagct gcagattcgg agtgcagacg agccgatgac cacattccta aaggtgggtg      60
cgcaccagcg gcttatgcgg ttctcatgca tctggcctga catgctttgc tgattgcggt     120
tgacagtgta ccacgtgtgg tgcccgatgg agagagaact gaagctactc cattattaga     180

| | |
|---|---|
| gttttggaaa tccctggaga acaatgtgtg ttgttcaaat aatagagggg cgggggataa | 240 |
| cgtagaggat gaacgcgaag ggtagaaggg gacacgaaaa aggaaggctg gtgctacggt | 300 |
| gtatgattag gacgatgatc tgggccccct gcgattgtga ttgttcccat ttgcgatgat | 360 |
| ttgcatctaa attactagag ataccctca atggatgatg acaccaatcc atagcactac | 420 |
| tatacaagag tggttaaact acacgcctac tccctattga gggagctaag aaaagtatgt | 480 |
| cagattaagc gcaaagaag aaattttctt cccgcctcgt tgatccaatt tatgattttt | 540 |
| tttttttttt tttttagta cttaattatt ttttgattaa ttttttttcgg ttcctatccc | 600 |
| cccctccta caaaatttgc cgccgcgaac atactctacg tactaactat tcatggtaac | 660 |
| ctggcaacgg caaataatgg cccgattggg attggccaga tccaggtaag ctaccaagtt | 720 |
| agtaggagta tagtactttg taggaaggat cctttgtgtg tgttgtttct ggtacggtac | 780 |
| caaatcttga gtcatttttt tttctcctct cttctcttat cctctaataa ccactgtcgg | 840 |
| ggtcccaaag aggaaggggt tggtcaaggg tgggaaaaga aaaagacaa aaatgagaga | 900 |
| aaagagaaag gctagatacc taaccgtact gtcaggtcaa gacactgagt gaggggcagt | 960 |
| gttgatggca aaaaagacg tgggcaagaa aaaagatttt ccctcacat gttttgccgc | 1020 |
| accagccatc ccactatcaa aaagcgatga tgtttgagat tgtcgggtgt ccacatctttt | 1080 |
| tagtgtgaat cgctagtaga atttgggata ttattgagca tcatcccatg atagcgagta | 1140 |
| caagccccga gtaaatacca acattgctat gctgctgtgc tgctatctag tttgctacgt | 1200 |
| tggtcgttga cctcacaggg atttccacca aaaagtggac cggcggcg ccactcggcc | 1260 |
| gtgccacagc agcctgagag cggacaaata acaacagccg cctgccgcgg ggttcggttg | 1320 |
| caaacatgac caacaggcca ggccatcatc aacccaccgc tgcgttgatg cccaggattt | 1380 |
| cagtccaata atccacaatt taccaacgga tagagctagg tgaattagat agacaggagg | 1440 |
| gccagaggga ggggaccgag atgaaaaatt ttcgatgaaa gagtggtcaa ggtgggtcg | 1500 |
| tagttcggcg ctccgagggc gaggaaccaa ggaaaggcga ggaaaggaca ggctgatcgc | 1560 |
| gctgcgttgc tgggctgcaa gcgtgtccag ttgagtctgg aaaaggctcc gccgtgaaga | 1620 |
| ttctgcgttg gtcccgcacc tgcgcggtgg gggcattacc cctccatgtc caatgatttc | 1680 |
| aagtcaaagc caagggttga agcccgcccg cttagtcgcc ttctcgcttg accctccat | 1740 |
| ataagtattt cccctcctcc ccctcccaca aattttccct ttccctttcc tccctcgtcc | 1800 |
| gcttcagtac gtatatcttc cccccctctc tcttccttct cactcttctc tccttctttc | 1860 |
| ttgattcatc ctctctctaa ctgacttctt tgctcagcac ctctacgcgt tctggccgta | 1920 |
| gtatctgagc aattttttcta cagacttttt ctatctaatt ccaaaaaaga acttcgagtt | 1980 |
| cattcacaac cgtcatcatg | 2000 |

<210> SEQ ID NO 2
<211> LENGTH: 2000
<212> TYPE: DNA
<213> ORGANISM: Aspergillus niger

<400> SEQUENCE: 2

| | |
|---|---|
| cctcaagctg tggcccagcc ttcctcaccc agccattttc gagctggttg gactccccaa | 60 |
| gtactacgac agtttgatcg aagaggccaa ccgtcggcgg tgcccaagt cgaagaagga | 120 |
| gcttagcgat cccagcatct gtctcttctg tggagatatt ttctgctcgc aggcagtatg | 180 |
| ctgcatggag aacaagctgg gcggatgcaa ccagcacgtt caaaagtagg tccattccca | 240 |
| cctctttggg gagtatctgg agaactcttc taacaacgaa tagatgtggc aagaatatcg | 300 |

```
gtttgttcat caacatccgc aagtgcactg tgctctactt gcacaaccac aatggatcat    360
ggcactacgc accgtacctt gaccgacatg gcgaggtcga cccgggtctc cggcgcaacc    420
gccagctgat cctcaaccag aagcgctacg accgacttct tcgggatgtg tggttgtcgc    480
acagcatccc ggccaccatc agtcggaagc tggaggcgga catcaacaac ggcgggtggg    540
agacgatcta gacattggtc cctgggagtt attgtgttcc gtgtttcagc attgttgtgt    600
atcctgattt ggcttgatga cccgtgccaa aagctcatga tgactttgca tgcattttat    660
cgaactgttt gttcttgaaa ataatttaca tatatgtatc tacgatgcag agggcccttg    720
ttcttgttga tggcggttga tactatatag tactctatgc gttgtgcttg gcgagattca    780
ctgatgctgt cggtaatggt tgtttgacag tgtgaatctt gatctgaatc gtgatttatc    840
ctatcctgca cactgaacta ggtattgatc tacatgtaga cctcgattcg aaaccagatc    900
agccgtgtga ctcacatgga gcgggtgtct cgcaaggata actttagccc tggtactagc    960
ccccatacgc actgtcatta gtgaggtgct gagacaattt aagcttttcgc ttcagccata   1020 gcttataaac agtaagatta tgagaggggg aaaagcttca accaagacta ttttcacccg   1080
tctttaggtt gttcataatg ggctacggct tcatggctct catgcctcca tcgtataatc   1140
gtcccttgta gacagtagcc agctacttac tagttagcac agtggacaca agccagcgaa   1200
tcggggtgaa gccaattagc attggatatc cacgaagtat gatcgtcacc ctccatgact   1260
tcacacggtt gctgcatcgg ttcaccgggt tgaacctagc cggcaggat cggagcaagt    1320 cgctggatcc ctcacggatc acagagctcc agctccacga agaaaagcag gatgcgatcc   1380
ccgcacatcg gagaattgca taccgttgaa gcaatccaag caattggcag gtgtcatctc   1440
cattacgtac cgtgaccttc ataccctccg tatttatacc tgcccctccc tcccccgctt   1500
ctcctgcttt cttcctctct ctttctctct tccatcaact caacttccat ctacttcact   1560
acttcctgtc aagtcttcca tcgactttca tcacaagtca tcctctccca tgtttgtatt   1620
ccctgtatag accgtactga cctcttccct agaaaccctc gtgcaatgta attccacctg   1680
cgtcggcccc tccccgggt ctcgtctcaa tacttcatta cacacgatgg aagtcatgca    1740
atgcctttgg ctggactctc tcaatgatca ggtatctcag gtaaatcttg ggcgtggacc   1800
ggtgttcgtt cctatccgtt ggttgtgcag cattgctagc attgctgcct gccatcggct   1860
ctgggttcgt tctgagatta tacggttaaa cttgatctgg ataataccag cgaaaggatc   1920
atgccttccc tcgtttcccc ccacttgatg gaatggctaa caattcccag tcccacctac   1980 cacacccttca aagcaacatg                                              2000
```

<210> SEQ ID NO 3
<211> LENGTH: 2000
<212> TYPE: DNA
<213> ORGANISM: Aspergillus niger

<400> SEQUENCE: 3

```
ctcagtcaat caactgacgg aattcatgtt caacttcacc cagaagagtc ggcgccagcg     60
gatcaaccag cggaaccgga cagagcgtct gagtgacctc ctggactgga aacgcatggg    120
ccttgagtat gtcaaggctc ggcagttggc actccgtcga ggtatgtgta tttccaagcc    180
actattgatt agattgctca cacgttcatg cagcctatcc ttcgtctttc ggcacgcctg    240
atgatgttta cgacgtaatc ggtggcacgg agcagaagat atcgcgacca ttatccgtac    300
ccggatcccc gcgagatcgt tctggtatga tgactcccgg ggattttgcc tctttgcagg    360
aggtgaaaga aggcctgagt acggaggact atgtcgcatg gcgactgccg taagtccacc    420
```

```
accccacccc cttgggtgaa tgaatgacac aaggagcgct gatgctgata aactggctgt      480
ctagaactag cgaggaagag gagccagatg accagtattt cccgctcacc ctgcgcacga      540
agaagaatac cgaccgtccg gcgtcgccgc tcgatcagct gtcggtcaat ggtgacagtt      600
gatcgactgg tgagatagcg cggtgcgaca gtctggaatt ctgaatagcc tgcatattcg      660
aggtaccgtt cttggtggaa tgatcgtgtt cgcgtttact tgctctcact aatcgcccgc      720
gtgtgaaata ctgcttttgg tcacccacct gctattgtta tccaaagcaa gcttcattca      780
gaaaagatgg tagctgattt agcccatcga gctctgatca gcatggcatt tcactttgtt      840
gttccatttt tttcatcttg cattgctcgt ttcctccatt cttgcattgt tttatcccct      900
ctttgcatat gtcatcactg ttgtagccag cgaattgtat cttctgattg gattctaccg      960
cagtaggtcc aggttgagat agtcgaatgc acgatgaata ttgtatccct acagtaacat     1020
accatcacga gctccgtgct cccgtccatc gtatccagcc cgccgacgcg gtaaccgata     1080
attcgtgctg ttgagagcga cgatgcacaa gcagctaggc tgatcatccg atccgaagca     1140
gagccaagca gatccttcct caagagtgtc tagacccgcc agccaggacc gaagacatcc     1200
ggttgttgag actagcctgg ccaaccatat agagttgagt cataataacc ttgtccgttg     1260
tgcttccgag cgggtctcga agcggggag aggatgagac aaggttcatg atgaggtggt     1320
tactgctgga gaaccggaaa agaacgccag gagcacacca ctccggcgac aggatctcca     1380
atgaggcatc tgcttcgttt tcgtgggggt cctggatgtg tttctcggtg agggaagacg     1440
acaatcgcgg atcctaactt agtagtgggg gtttagtcca gggtctcgct tgaccccgct     1500
gcttcccatt tatgccacgt cttctccctc ctctctcgct tgctttcctt tcccttcatc     1560
ttcccatctt ctcactatct atcttcagtt atattgtttc cgaataactt acttcttctt     1620
ccccaacaac ttcctcgtta accgtccggt acgactcaca atgaggccgc gcacgcagga     1680
tcagactccg ggtctttcg ctatgggttc agatgggtca aggtatcgta caatagtata     1740
acagtcactg ctcgcgcatg acaggtgttc ggctcgtgct tctgttcctt tccttctggt     1800
ttggacagga gcgcggtcgt tctgagatta tactgtcaaa acttgatcta gataatacta     1860
gcgaaaggac atgcgtggca ctgattgtcc cctactattt gacctacaga agacgagagg     1920
gatctcgcat ccctctctgt tgctgacagt ttccagacct ttgcaattac cctcgacctg     1980
agtgtatttg tgccaaaatg                                                2000

<210> SEQ ID NO 4
<211> LENGTH: 2000
<212> TYPE: DNA
<213> ORGANISM: Aspergillus niger

<400> SEQUENCE: 4
ttccaacaac tttaacccaa tcaacatgct acaaatccca attttgacca cacccaagac       60
acctaaacca cacccgaacc taccgttgct ggcacaacag gcgtagatga aggtggtat      120 ccccatgttt tttagcgggt gggtcccgga cgaaaaggaa agagtttgtc aggtttgccc      180
gccccgtcga acaaacaaaa agatcaagaa ttaaaaataa aaattgaaaa aaaaggagga      240
aaggaagaag aaaatcgaaa gacagaaaga ggaggaccaa ggtggaaaat gaaactagtc      300
acattcgagc agaaacagtg ggtcccggct ggaacaattc ctgtttgggt aatgtaggtc      360
tcgtgtcttc tttggctgca tacgaaaata tgatgccggc acctgaaaag tgtggaagaa      420
tatctggatc ggacagatac actggtcgcg tgtatatctc ttgtatctac tgatatagcg      480
tggctattca gaacatgaag agtggtgata attgaatcaa ttacccctta gcacgcacat      540
```

| | |
|---|---:|
| aagactacta cctgcgatct tcggacacta ggatgaggga taaaaaggag tacggtctga | 600 |
| ggtatataac ctctaggaac aagcatatgc tactgctgtg cccttgccta cgaaatgcag | 660 |
| catagccatg tagtgtactc cgtagaaaaa ctaagcttgg acaatagcga ctgtatttta | 720 |
| accggagaga gtatgataga gaccaaccta tgggatactt catattaccg acgttgcccg | 780 |
| tgtttgcgat cgctcccctg gccgcccccct tctgtctctc tctctcgctc tctctccgta | 840 |
| cctgagaact tccgcccgga gcaagaaaaa cggggaaatc gcggcatgtc agccgaaaga | 900 |
| cgccgcacgc acctgatcag tcccggtggc gcgtatgaag gcccagaaac cgtggactcc | 960 |
| gtttggatgc tgcagataga taagtagtag cgtagatatt taagtaactg agttttgtga | 1020 |
| gttgtcttca aacaatttct acacaggagg ccgatgcaaa tttacaattt cggtcttgca | 1080 |
| attgtcgttg tgcacgagta agtcaagtac acagtaggag gctgagaggc aagcgttttg | 1140 |
| ccatcggata tccgggacca gatgaaagaa aggggcggtt ccccatggat ggagcgcgaa | 1200 |
| ggtgtggact ccaagaaaac gctttggttc ggtcaagacg gggaaatggg agaggaatgg | 1260 |
| atatcttacg aagccgaatt acggagaaag ggcccaaaca tgtaaattat ggcctgtagg | 1320 |
| tcaatcagca aagggccgag cggtgattgc gagtacaccg atcggtagac tacgaagggg | 1380 |
| atgaaaaaga caggaaaata gcgagagcta catgccgttt cagaggctat cgaaatgata | 1440 |
| ttccaaagta tcaccagtag ccataaccac tataataaag gacgaagatg agagtgcctt | 1500 |
| cgttctcttt gaccagaaat tcactcatag tatcaagggg tatttcccaa taatgtcagc | 1560 |
| ggtcggagtt ggttactggc gcgatcggga gatatcggct cttcgttgcc tgggccagca | 1620 |
| ttagcgccgg gtccaggttt tttttttgca aattttttttt tcttttcctg gctatgtttt | 1680 |
| ttttcgttcc ccctaacaat gggaaggacc tccctactcc gtaccgggcc aaccaatccg | 1740 |
| gccaatggaa actgggccgg gacgcccatc gccgccgctg ccactgcaaa ttcaggccag | 1800 |
| cgaaaaaccc aagagcgtcc tagcgtctcc gctcgcttct tcccgcttac aagagccctt | 1860 |
| cgctcgctat ttttttcttcc ctcccttccc ttctctcttc ttttcttttcc atcccctttg | 1920 |
| aagtgtcctg tttgactggc actatcatcc atctcctctc tttctttcct tagttttcgt | 1980 |
| tcatcacagc cgtcaaaatg | 2000 |

<210> SEQ ID NO 5
<211> LENGTH: 2000
<212> TYPE: DNA
<213> ORGANISM: Aspergillus niger

<400> SEQUENCE: 5

| | |
|---|---:|
| gaccgacctc ggaaatggat aggttaggaa aattgggggg gaagggccac acaaaaaatt | 60 |
| agcaagaaat taggagaaga gtgaaagaat tttgccccgg aatcctctcc ctgatccagg | 120 |
| tataagtagc agacggatgt cttcttggga agatgggaag aaaaacgggc tgcaggtga | 180 |
| gcaagaggat aaaaattaca caatgggttc ccgaagggat tctcttggtg gaaaggggtg | 240 |
| gtggccacga taacaagcaa caacactgca gggaaaaacc gcgagcaagc cagccactag | 300 |
| cggctgactg tgtgggatat gctttcgtcc ggttttccag aggccacggg atgatgtcga | 360 |
| tgggagggat tgggttggct tgcgccgcgc cgcccacttt tctcccctat ccagcttgcg | 420 |
| ccgcgccgac ccccccctga gatttgctcc ttattccccc gagagggatc aatttctctg | 480 |
| atgtatccaa aaagctatat aacccgtgca ccacccacgg agacaagcgc gctgaggcat | 540 |
| tgggggaagt cgtttttttt ttttctacca tagcgccaga ggtgtgtgga ctaacatttc | 600 |
| tgtgctattt gcgagctagc tcagggagct acggatcgtc gcgcgttttcc ccggcgaaag | 660 |

```
gcgctccgta cggagccggg ttgtcccaaa acggcagata cccaatacga tgagtcggtg    720
aggcatttcc cgagggagca gaccaggagc acagcaacag aacacaattg gggaagcttc    780
cctccttcca gccgacgcgg cgcaaacctg cttgcgtctc agaagtggga attttcttgc    840
tcagaaactc cggtgctggt ggagccgcat gcccgattcg gcccggtttg attgcgaccg    900
agaagctggc catcatatta gctgggcctt ggctgcttcc cattggcttc cgggacaccg    960
ccaagtgggg gtgtaccact ctatcggacc catttggatg cagggaccca cccgcacgtc   1020
tggttttttc ccttctttgc ggtctcccgt tttgctgtga aaattttgca taccgtagct   1080
ggtctctatt gcttgtctct tgtcttgtcc tgtcttttcc ggtctgttgc tgggttaggt   1140
ggcccggtgt cagaagcgga agggagaagg ggacaattta tatgtaagga aagaatgaag   1200
ggagggaccc gtagagacaa gacaagaatg ttttttctc tccttttgt gacgacacga     1260 gggaaaaaag gaattgaacg gaagggatcg gttcatacaa gtgtaaaata cacacacgac   1320
tacggaataa tcccatcaga tgcagcaatg ggttatctga aggggaagga gatgtgtgag   1380
tgaatgagag agtaagccaa tgctccatcg cggaccagca cggtcaggtg aagaccctga   1440
aaccattggc tgtaccagta gtaactcccc tggttacccc catcccgagt gatcccgaag   1500
ggtgtgtatg tgtgtatgtg tacacagtat gtgtaaggaa gtgtggtaag tgtgtatgtg   1560
cggtggaatg cccactgctt tcccgggga aggaaaaagg atgatgagcc aaaaacgagg    1620
cgccaaacac ggtgtaaggg aaaaagaagg gaaaggataa actagggata acggatgata   1680
ccaaagacag acacaaacag gaaaaacagg aacaatacaa tacaaacaaa cggtgccaaa   1740
acaccaaaca aaaagtagg tagggctttt ttttctggtc ccaacaaagc gcactaacac    1800
ccgacggggg ggctgggtgg gaaaagggca aaaaccgcg aaaatttagc gggagagtat    1860
ttatgtcccg gggggccttc tgttgtcact tttcctccag cttttttcctc cagaaaagtt  1920 ctccttcctt ctttcccttc ccaatcccat cattttctag agaaactcct ctctcagaac   1980
caccacaaac catcacaatg                                               2000
```

<210> SEQ ID NO 6
<211> LENGTH: 63
<212> TYPE: DNA
<213> ORGANISM: Artificial Sequence
<220> FEATURE:
<223> OTHER INFORMATION: Oligonucleotide designed as PCR primer to
      generate a DNA fragment in the polymerase chain reaction

<400> SEQUENCE: 6

```
atgcggccgc ctcgagttaa ttaaggccag gccggccggc gcgcctcagc aatgtcgttc    60
cga                                                                  63
```

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide designed as primer to generate
      a DNA fragment in the polymerase chain reaction

<400> SEQUENCE: 7

```
agccattgac ttcttcccag                                                20
```

<210> SEQ ID NO 8
<211> LENGTH: 28
<212> TYPE: DNA
<213> ORGANISM: Artificial Sequence
<220> FEATURE:
<223> OTHER INFORMATION: Oligonucleotide designed as primer to generate
      a DNA fragment in the polymerase chain reaction

<400> SEQUENCE: 8
atctcgagag attcggagtg cagacgag                                        28

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide designed as primer to generate
      a DNA fragment in the polymerase chain reaction

<400> SEQUENCE: 9
atggcgcgcc cggttgtgaa tgaactcgaa                                      30

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide designed as primer to generate
      a DNA fragment in the polymerase chain reaction

<400> SEQUENCE: 10
atctcgagct tcctcaccca gccattt                                         27

<210> SEQ ID NO 11
<211> LENGTH: 30
<212> TYPE: DNA
<213> ORGANISM: Artificial Sequence
<220> FEATURE:
<223> OTHER INFORMATION: Oligonucleotide designed as primer to generate
      a DNA fragment in the polymerase chain reaction

<400> SEQUENCE: 11
atggcgcgcc agggtgtggt aggtgggact                                      30

<210> SEQ ID NO 12
<211> LENGTH: 30
<212> TYPE: DNA
<213> ORGANISM: Artificial Sequence
<220> FEATURE:
<223> OTHER INFORMATION: Oligonucleotide designed as primer to generate
      a DNA fragment in the polymerase chain reaction

<400> SEQUENCE: 12
atctcgagtc aactgacgga attcatgttc                                      30

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide designed as primer to generate
      a DNA fragment in the polymerase chain reaction

<400> SEQUENCE: 13
atggcgcgcc ggtcgagggt aattgcaaag                                      30

<210> SEQ ID NO 14
<211> LENGTH: 28
<212> TYPE: DNA
<213> ORGANISM: Artificial Sequence
<220> FEATURE:
<223> OTHER INFORMATION: Oligonucleotide designed as primer to generate

```
                                         -continued a DNA fragment in the polymerase chain reaction

<400> SEQUENCE: 14
atctcgagtt ttgaccacac ccaagaca                                              28

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide designed as primer to generate
        a DNA fragment in the polymerase chain reaction

<400> SEQUENCE: 15
atggcgcgcc ttttgacggc tgtgatgaac                                            30

<210> SEQ ID NO 16
<211> LENGTH: 28
<212> TYPE: DNA
<213> ORGANISM: Artificial Sequence
<220> FEATURE:
<223> OTHER INFORMATION: Oligonucleotide designed as primer to generate
        a DNA fragment in the polymerase chain reaction

<400> SEQUENCE: 16
atctcgagac cgacctcgga aatggata                                              28

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide designed as primer to generate
        a DNA fragment in the polymerase chain reaction

<400> SEQUENCE: 17
atggcgcgcc ttgtgatggt ttgtggtggt                                            30
```